United States Patent [19]
Kehry et al.

[11] Patent Number: 5,817,516
[45] Date of Patent: Oct. 6, 1998

[54] METHODS FOR PROLIFERATING AND DIFFERENTIATING B CELLS WITH HIGH DENSITY MEMBRANE CD40 LIGAND

[75] Inventors: Marilyn Kehry, Danbury; Brian Castle, New Fairfield, both of Conn.

[73] Assignee: Boehringer Ingelheim Pharmaceuticals, Inc., Ridgefield, Conn.

[21] Appl. No.: 431,055

[22] Filed: Apr. 28, 1995

Related U.S. Application Data

[63] Continuation-in-part of Ser. No. 234,580, Apr. 28, 1994, abandoned.

[51] Int. Cl.$^6$ .............................. C12N 5/02; C12N 5/08
[52] U.S. Cl. .............................. 435/377; 435/2; 435/325; 435/366; 435/372.2; 435/375
[58] Field of Search .............................. 435/2, 7.1, 7.21, 435/240.1, 240.2, 240.21, 240.25, 325, 375

[56] References Cited

PUBLICATIONS

1. Hollenbaugh et al. EMBO J. 11: 4313–4321 (1992).
2. Spriggs et al. J Exp Med 176: 1543–1550 (1992).
①  Castle et al. FAJEB J. 8: A 1012 (1994).

Armitage et al., "Human B Cell Proliferation and Ig Secretion Induced by Recombinant CD40 Ligand Are Modulated by Soluble Cytokines", J. Immunology, vol. 150, No. 9: 3671–3680 (1993) (May issue).

Armitage et al., "CD40L: A Multifunctional Ligand", Sem. Immunol. 5:401–412 (1993) (Dec. issue).

Marshall et al., "The Molecular Basis for T Cell Help in Humoral Immunity: CD40 and Its Ligand, gp39", J. Clin. Immunol. 13(3): 165–174 (1993) (Jun. issue).

Maliszewski et al., "Recombinant CD40 Ligand Stimulation of Murine B Cell Growth and Differentiation: Cooperative Effects of Cytokines", Eur. J. Immunol. No. 5: 23:1044–1049 (1993) (May issue).

1. Kehry et al. "B Cell Activation Mediated By Interactions With Membranes From Helper Cells", in Mechanisms of Lymphocyte Activation and Immune Regulation IV: Cellular Communications, pp. 139–148 (S. Gupta et al. Eds., 1992).

*Primary Examiner*—Lila Feisee
*Assistant Examiner*—Phillip Gambel
*Attorney, Agent, or Firm*—Sterne Kessler Goldstein & Fox P.L.L.C.

[57] ABSTRACT

The present invention provides methods of proliferating B cells as a means of obtaining large numbers of B cells. The present invention further provides methods of differentiating a proliferating B cell population to antibody producing cells.

14 Claims, 16 Drawing Sheets

Murine

CTTTCAGTCA GC ATG ATA GAA ACA TAC AGC CAA CCT TCC CCC AGA TCC
              Met Ile Glu Thr Tyr Ser Gln Pro Ser Pro Arg Ser

GTG GCA ACT GGA CTT CCA GCG AGC ATG AAG ATT TTT ATG TAT TTA CTT
Val Ala Thr Gly Leu Pro Ala Ser Met Lys <u>Ile Phe Met Tyr Leu Leu</u>

ACT GTT TTC CTT ATC ACC CAA ATG ATT GGA TCT GTG CTT TTT GCT GTG
<u>Thr Val Phe Leu Ile Thr Gln Met Ile Gly Ser Val Leu Phe Ala Val</u>
                        TM

TAT CTT CAT AGA AGA TTG GAT AAG GTC GAA GAG GAA GTA AAC CTT CAT
<u>Tyr Leu</u> His Arg Arg Leu Asp Lys Val Glu Glu Glu Val Asn Leu His

GAA GAT TTT GTA TTC ATA AAA AAG CTA AAG AGA TGC AAC AAA GGA GAA
Glu Asp Phe Val Phe Ile Lys Lys Leu Lys Arg Cys Asn Lys Gly Glu

GGA TCT TTA TCC TTG CTG AAC TGT GAG GAG ATG AGA AGG CAA TTT GAA
Gly Ser Leu Ser Leu Leu Asn Cys Glu Glu Met Arg Arg Gln Phe Glu

GAC CTT GTC AAG GAT ATA ACG TTA AAC AAA GAA GAG AAA AAA GAA AAC
Asp Leu Val Lys Asp Ile Thr Leu Asn Lys Glu Glu Lys Lys Glu Asn

AGC TTT GAA ATG CAA AGA GGT GAT GAG GAT CCT CAA ATT GCA GCA CAC
Ser Phe Glu Met Gln Arg Gly Asp Glu Asp Pro Gln Ile Ala Ala His

GTT GTA AGC GAA GCC AAC AGT AAT GCA GCA TCC GTT CTA CAG TGG GCC
Val Val Ser Glu Ala Asn Ser Asn Ala Ala Ser Val Leu Gln Trp Ala

AAG AAA GGA TAT TAT ACC ATG AAA AGC AAC TTG GTA ATG CTT GAA AAT
Lys Lys Gly Tyr Tyr Thr Met Lys Ser Asn Leu Val Met Leu Glu Asn

GGG AAA CAG CTG ACG GTT AAA AGA GAA GGA CTC TAT TAT GTC TAC ACT
Gly Lys Gln Leu Thr Val Lys Arg Glu Gly Leu Tyr Tyr Val Tyr Thr

CAA GTC ACC TTC TGC TCT AAT CGG GAG CCT TCG AGT CAA CGC CCA TTC
Gln Val Thr Phe Cys Ser Asn Arg Glu Pro Ser Ser Gln Arg Pro Phe

ATC GTC GGC CTC TGG CTG AAG CCC AGC ATT GGA TCT GAG AGA ATC TTA
Ile Val Gly Leu Trp Leu Lys Pro Ser Ile Gly Ser Glu Arg Ile Leu

FIG. 1A

```
CTC AAG GCG GCA AAT ACC CAC AGT TCC TCC CAG CTT TGC GAG CAG CAG
Leu Lys Ala Ala Asn Thr His Ser Ser Ser Gln Leu Cys Glu Gln Gln

TCT GTT CAC TTG GGC GGA GTG TTT GAA TTA CAA GCT GGT GCT TCT GTG
Ser Val His Leu Gly Gly Val Phe Glu Leu Gln Ala Gly Ala Ser Val

TTT GTC AAC GTG ACT GAA GCA AGC CAA GTG ATC CAC AGA GTT GGC TTC
Phe Val Asn Val Thr Glu Ala Ser Gln Val Ile His Arg Val Gly Phe
            --- CHO ---
TCA TCT TTT GGC TTA CTC AAA CTC TGAACAGTGC GCTGTCCTAG GCTGCA      818
Ser Ser Phe Gly Leu Leu Lys Leu END                               260
```

Human

```

CCATTTCAAC TTTAACACAG C ATG ATC GAA ACA TAC AAC CAA ACT TCT CCC
                       Met Ile Glu Thr Tyr Asn Gln Thr Ser Pro
                                        --- CHO ---
CGA TCT GCG GCC ACT GGA CTG CCC ATC AGC ATG AAA ATT TTT ATG TAT
Arg Ser Ala Ala Thr Gly Leu Pro Ile Ser Met Lys Ile Phe Met Tyr

TTA CTT ACT GTT TTT CTT ATC ACC CAG ATG ATT GGG TCA GCA CTT TTT
Leu Leu Thr Val Phe Leu Ile Thr Gln Met Ile Gly Ser Ala Leu Phe

GCT GTG TAT CTT CAT AGA AGG TTG GAC AAG ATA GAA GAT GAA AGG AAT
Ala Val Tyr Leu His Arg Arg Leu Asp Lys Ile Glu Asp Glu Arg Asn

CTT CAT GAA GAT TTT GTA TTC ATG AAA ACG ATA CAG AGA TGC AAC ACA
Leu His Glu Asp Phe Val Phe Met Lys Thr Ile Gln Arg Cys Asn Thr

GGA GAA AGA TCC TTA TCC TTA CTG AAC TGT GAG GAG ATT AAA AGC CAG
Gly Glu Arg Ser Leu Ser Leu Leu Asn Cys Glu Glu Ile Lys Ser Gln

TTT GAA GGC TTT GTG AAG GAT ATA ATG TTA AAC AAA GAG GAG ACG AAG
Phe Glu Gly Phe Val Lys Asp Ile Met Leu Asn Lys Glu Glu Thr Lys

AAA GAA AAC AGC TTT GAA ATG CAA AAA GGT GAT CAG AAT CCT CAA ATT
Lys Glu Asn Ser Phe Glu Met Gln Lys Gly Asp Gln Asn Pro Gln Ile

GCG GCA CAT GTC ATA AGT GAG GCC AGC AGT AAA ACA ACA TCT GTG TTA
Ala Ala His Val Ile Ser Glu Ala Ser Ser Lys Thr Thr Ser Val Leu
```

FIG. 1B

```
CAG TGG GCT GAA AAA GGA TAC TAC ACC ATG AGC AAC AAC TTG GTA ACC
Gln Trp Ala Glu Lys Gly Tyr Tyr Thr Met Ser Asn Asn Leu Val Thr

CTG GAA AAT GGG AAA CAG CTG ACC GTT AAA AGA CAA GGA CTC TAT TAT
Leu Glu Asn Gly Lys Gln Leu Thr Val Lys Arg Gln Gly Leu Tyr Tyr

ATC TAT GCC CAA GTC ACC TTC TGT TCC AAT CGG GAA GCT TCG AGT CAA
Ile Tyr Ala Gln Val Thr Phe Cys Ser Asn Arg Glu Ala Ser Ser Gln

GCT CCA TTT ATA GCC AGC CTC TGC CTA AAG TCC CCC GGT AGA TTC GAG
Ala Pro Phe Ile Ala Ser Leu Cys Leu Lys Ser Pro Gly Arg Phe Glu

AGA ATC TTA CTC AGA GCT GCA AAT ACC CAC AGT TCC GCC AAA CCT TGC
Arg Ile Leu Leu Arg Ala Ala Asn Thr His Ser Ser Ala Lys Pro Cys

GGG CAA CAA TCC ATT CAC TTG GGA GGA GTA TTT GAA TTG CAA CCA GGT
Gly Gln Gln Ser Ile His Leu Gly Gly Val Phe Glu Leu Gln Pro Gly

GCT TCG GTG TTT GTC AAT GTG ACT GAT CCA AGC CAA GTG AGC CAT GGC
Ala Ser Val Phe Val Asn Val Thr Asp Pro Ser Gln Val Ser His Gly
                        --- CHO ---
ACT GGC TTC ACG TCC TTT GGC TTA CTC AAA CTC TGAACAGTGT CACCTTGCAG
Thr Gly Phe Thr Ser Phe Gly Leu Leu Lys Leu END                           261

GCTGTGGTGG AGCTGA                                                         840
```

FIG.1C

METHODS FOR PROLIFERATING AND DIFFERENTIATING B CELLS WITH HIGH DENSITY MEMBRANE CD40 LIGAND

CROSS-REFERENCE TO RELATED APPLICATION

This application is a continuation-in-part of U.S. application Ser. No. 08/234,580, filed Apr. 28, 1994, now abandoned, the contents of which are incorporated herein by reference.

BACKGROUND OF THE INVENTION

1. Field of the Invention

The present invention is direct to the field of immunology. Specifically, the present invention provides methods for proliferating and differentiating B cells.

2. Related Art

During an immune response, activation and differentiation of B cells lead to the secretion of high affinity antigen-specific antibodies. When the antibody response is directed against protein antigens the production of antibodies is also dependent on the activation of specific helper T (Th) cells and their interactions with B cells. During the processes of activation and differentiation, B cells follow one or more distinct and irreversible pathways to acquire one of several identifiable functionalities. For example, initially activated B cells undergo high levels of proliferation, and during this period of cell division several different events can occur: isotope switching can occur to give recombination of heavy chain variable (V) region genes proximal to different constant regions ($\gamma$ subclasses, $\alpha$, or $\epsilon$) and secretion of different antibody classes; somatic mutation can occur in the heavy and light chain V region gene segments to generate high affinity antibody combining sites; and B cells can differentiate to become memory cells or efficient antibody secreting plasma cells.

Which pathway(s) a particular B cell follows is most likely determined by the types of stimuli it receives; this is presumably determined by its overall milieu. For example, the presence of other cell types (different types of Th cells and/or follicular dendritic cells) and the presence or absence of specific antigen may deliver different signals to B cells. Some events, such as the signals that generate memory B cells and the molecular mechanisms that drive somatic mutation and selection of high affinity antibody producing cells, are poorly understood. Other processes, such as initial activation signals that drive naive B cells to proliferate and which are provided by contact with specific primed and activated Th cells have now been well characterized. (Parker, D., *Annu. Rev. Immunol.* 11:331–360 (1993)). Additionally, the effects of soluble Th cell-derived lymphokines on activated B cells have also been delineated (Parker, D., *Annu. Rev. Immunol.* 11:331–360 (1993); Hodgkin et al., *J. Immunol.* 145:2025–2034 (1990); Noelle et al., *J. Immunol.* 146:1118–1124 (1991)).

Because the generation of primed and activated Th cells is obligatory for B cell activation, defining the requirements of B cells themselves using classical in vitro systems employed for studying B cell responses has been difficult. In these systems, many of which utilized purified B cells, antigen-specific Th cell clones, and antigen, requirements for Th cell activation also were essential for generating a B cell response.

I. Contact-Dependent Delivery of Signals from Th Cells to B Cells

The steps involved in B cell activation by Th cells can be divided into first, the major histocompatibility complex (MHC)-restricted activation and priming of specific Th cells, and second, the interaction of secondary activated Th cells with B cells to induce B cell activation, proliferation, and differentiation. (Parker, D., *Annu. Rev. Immunol.* 11:331–360 (1993)). Naive Th cells are primed by interactions with antigens that have been cleaved into peptides (processed) which have bound to class II MHC molecules on the surface of antigen presenting cells. At the Th cell priming stage, resting B cells are not able to serve as antigen presenting cells because they do not appear to be capable of providing necessary costimulatory signals to the Th cells. Antigen presenting cells that can provide appropriate costimulatory signals for Th cell priming are interdigitating dendritic cells found in the T cell rich areas of the spleen and possibly activated B cells. Once specific Th cells are primed, their activation requirements appear to be less stringent. Primed Th cells can be efficiently activated by resting B lymphocytes that have captured antigen with specific antigen receptors and processed it to peptides. (Parker, D.,*Annu. Rev. Immunol.* 11:331–360 (1993)). Once activated, primed Th cells express genes that enable them to reciprocally deliver appropriate contact- and lymphokine-dependent activation signals to resting B cells. (Kehry, M. R., and Hodgkin, P. D., *Sem. Immunol.* 5:393–400 (1993)).

II. Historical Perspective

Several studies in the 1980's described critical features of specific signals delivered by activated primed Th cells to B cells. (Coffman et al., *Immunol. Rev.* 102:5–28 (1988); DeFranco et al., *J. Exp. Med.* 159:861–880 (1984)). B cell-Th cell contact was required; the Th cell-derived signals that drive resting B cell activation could not be replaced by soluble lymphokines alone (Andersson et al., *Proc. Natl. Acad. Sci. USA* 77:1612–1616 (1980); Julius et al., *Proc. Natl. Acad. Sci. USA* 79:1989–1993 (1982); Owens, T., *Eur. J. Immunol.* 18:395–401 (1988); Whalen et al.,*J. Immunol.* 141:2230–2239 (1988); Hirohata et al., *J. Immunol.* 140:3726–3744 (1988); Noelle et al., *J. Immunol.* 140:1807–1814 (1989); Julius et al., *Eur. J. Immunol.* 18:381–386 (1988)). A finding important in characterizing the molecules involved in delivering contact signals to resting B cells was that preactivated Th cells could be employed to deliver activation signals. This implied that the contact signals received by naive B cells did not need to be cognate; they were antigen independent and were not MHC restricted. The B cell activating signals appeared to be different from signals required for Th cell activation and were thus capable of generating significant bystander B cell responses. (Whalen et al., *J. Immunol.* 141:2230–2239 (1988)). This suggested that the B cell receptors for Th cell-dependent contact signals were constitutively expressed and were not polymorphic or related to the B cell antigen receptor. Additionally, the Th cell molecules delivering the contact signals were most likely not functionally present in resting Th cells. This rules out a role for the T cell receptor complex that was initially involved in receiving antigen-specific Th cell activation signals.

These studies also delineated a role for Th cell-derived lymphokines in determining the amount and isotope of antibody secreted. (Coffman et al., *Immunol. Rev.* 102:5–28 (1988)). In the mouse, the ability of a Th cell clone to induce B cell differentiation has been shown to depend on the repertoire of lymphokines secreted after its activation. Th2 type Th cell clones, that secrete IL-4 and IL-5, are effective in inducing production of IgM and switching to IgG1, IgA, and IgE (Coffman et al., *Immunol. Rev.* 102:5–28 (1988); Mosmann & Coffman, *Annu. Rev. Immunol.* 7:145–173 (1989)). Although some controversy initially existed about the ability of Th1 type Th cell clones, that produce IL-2 and IFN-γ, to stimulate B cell differentiation, it appears that most Th1 cell clones are capable of providing the appropriate contact and soluble signals to activate resting B cells to secrete antibody when Th2 lymphokines are provided. (Abbas et al., *J. Immunol.* 144:2031–2037 (1990)).

Although the role of lymphokines seemed to be inducing B cell differentiation and not in initiating activation events, a system that separately delivered Th cell contact from soluble signals was needed. An early study demonstrated that membrane components from T cells could be transferred to other cell types by a Sendai virus-mediated fusion event. (Lindqvist et al., *Scand. J. Immunol.* 23:119–125 (1986)). These cells contained functional T cell-specific membrane proteins that could transduce signals for the activation of T cell-specific genes, but the cells were not examined for the ability to activate B cells. An additional study demonstrated that tumor cell plasma membranes were sufficient to generate allogeneic cytotoxic T lymphocytes (Stallcup et al., *Cell. Immunol.* 89:144–150 (1984)). This suggested that cell—cell contact provided critical signals that regulated lymphocyte activation. However, high doses of plasma membranes were nonspecifically inhibitory to both T and B lymphocyte responses (Stallcup et al., *Cell. Immunol.* 89:144–150 (1984)). Several years later, Sekita et al. prepared plasma membranes from a variety of T cell and lymphoid cell lines and demonstrated their ability to stimulate and costimulate B cell proliferation (Sekita et al., *Eur. J. Immunol.* 18:1405–1410 (1988)). However, these investigators found that membranes prepared from most cell types could activate B cells (Sekita et al., *Eur. J. Immunol.* 18:1405–1410 (1988)). Since no specificity was observed for Th cells or for activated over resting T cells, the active component in those membranes appeared to be different from that induced by activation of normal primed Th cells.

Studies that showed the most promise for developing a Th cell-free system for delivering contact signals to B cells used a plasma membrane-enriched fraction of vesicles prepared from an activated mouse Th2 cell clone, D10.G4.1 (D10), to deliver contact signals in the absence of other cell types (Brian, A. A., *Proc. Natl. Acad. Sci. USA* 85:564–568 (1988)). In this work, specificity was demonstrated in that membranes prepared from resting Th2 cells were not stimulatory for B cell proliferation. However, the B cell population had not been purified to eliminate preactivated B cells, which have different activation requirements than resting B cells. Preactivated B cells respond to Th2 lymphokines alone (in particular, IL-5) by growing and secreting IgM in the absence of Th cell-dependent contact signals (Takatsu et al., *Immunol. Rev.* 102:107–135 (1988)). Because it is not possible to separate contaminating endoplasmic reticulum vesicles that would contain lymphokines from plasma membrane vesicles it was not clear in the initial work (Brian, A. A., *Proc. Natl. Acad. Sci. USA* 85:564–568 (1988)) whether an actual contact-dependent stimulus could be delivered to resting B cells by a plasma membrane fraction from a Th cell clone.

SUMMARY OF THE INVENTION

The present invention is based on the observation that high density, membrane bound CD40 ligand (hereinafter, hdmb CD40 ligand), can induce long term proliferation of B cells in culture. In addition, it has been found that by varying the types and concentration of lymphokines and/or contact cells which are present during proliferation, proliferating B cells can be induced to differentiate (mature) into antibody producing cells. Lastly, it has been observed that proliferation and differentiation in the presence of an antigen preferentially proliferates or selects differentiating populations of B cells to increase the percentage of cells which produce antibodies specific to the antigen supplied.

Based on the above observations, one embodiment of the present invention provides methods for proliferating B cells which comprise the step of culturing one or more B cells in the presence of hdmb CD40 ligand. The procedures of the present invention can be applied to B cells isolated from any mammal, the most preferred being human B cells.

The presently claimed methods improve previous attempts to proliferate B cells in the use of hdmb CD40 ligand. Previous attempts at proliferating B cell populations in the presence of naturally isolated membrane bound CD40 ligand, membrane bound CD40 ligand produced from transfected animal cells, recombinantly produced soluble forms of CD40 ligand, and anti-CD40 receptor antibodies have yielded poor results. Proliferation tends to be moderate, ending after 1–4 rounds of replication, and there is often a requirement for the presence of a lymphokine or cytokine (for example Th lymphokines) to stimulate proliferation. Using the present methods, proliferation responses as great as 250-fold, have been obtained.

The present method can be used in a single step proliferation procedure or in a multi-step procedure. Specifically, hdmb CD40 ligand is included in the culture media during the initial phases of culturing. The presence of hdmb CD40 ligand is maintained until the rate of proliferation decreases. The cells are then rested by culturing under conditions which do not contain hdmb CD40 ligand. After resting the cells, the cells can be restimulated to continue proliferation and differentiation by adding the hdmb bound CD40 ligand and cytokines back to the culture media.

A further embodiment of the present invention is based on the observation that cytokines, extracts from cells, and/or selected feeder cells when added to B cells which are proliferating or have been proliferated using the above described methods, stimulate the B cells to differentiate into antibody producing cells. Based on this observation, the present invention provides methods for differentiating proliferating B cells comprising the step of culturing B cells in the presence of hdmb CD40 ligand and one or more lymphokines, feeder cells, or extracts thereof. Examples of the cytokines and feeder cells which can be employed include, but are not limited to Th2 lymphokines and follicular dendritic cells.

A third embodiment of the present invention is based on the observation that the differentiation of B cells can be partially controlled by including an antigen in the culture media. Specifically, the percentage of B cells which produce antibodies selective for a specific antigen can be increased by adding an antigen to the culture media during the proliferation stage, the resting stage, the differentiation stage, or the reproliferation stage of the herein described methods.

In addition to in vitro use, other forms of the CD40 ligand have been described in the literature as providing means of proliferating and activating B cells within a mammalian host. In general, pathological conditions which result in the suppression of B cell proliferation and activation can be treated using the hdmb CD40 ligand of the present invention in place of the previously generated forms of CD40 ligand.

By supplying a mammal with hdmb CD40 ligand, B cell populations can be proliferated within the host to a level and at a rate which is much greater than that found with previously isolated forms of CD40 ligand.

BRIEF DESCRIPTION OF THE FIGURES

FIG. 1 DNA Sequence of Mouse and Human CD40 and CD40 Ligand

The nucleotide sequences of human and mouse CD40 ligand. CD40 is a member of the TNF receptor family (Mallett & Barclay, *Immunol. Today* 12:220–223 (1991)) containing four repeating Cys-rich extracellular domains. The mouse CD40 ligand is a 33,000–35,000 MW type 2 membrane glycoprotein predicted to be 260 amino acids in length and expressed on activated T cells. It is related to TNF (Farrah & Smith, *Nature* 358:26 (1992)) and ligands for other members of the TNF receptor family (Goodwin et al., *Cell* 73:447–456 (1993); Smith et al., *Cell* 73:1349–1360 (1993); Smith et al., *Cell* 76:959–962 (1994); Aruffo et al., *EMBO J.* (1992); Hollenbaugh et al., *EMBO J.* 11:4313–4321 (1992)).

Figure 2A:
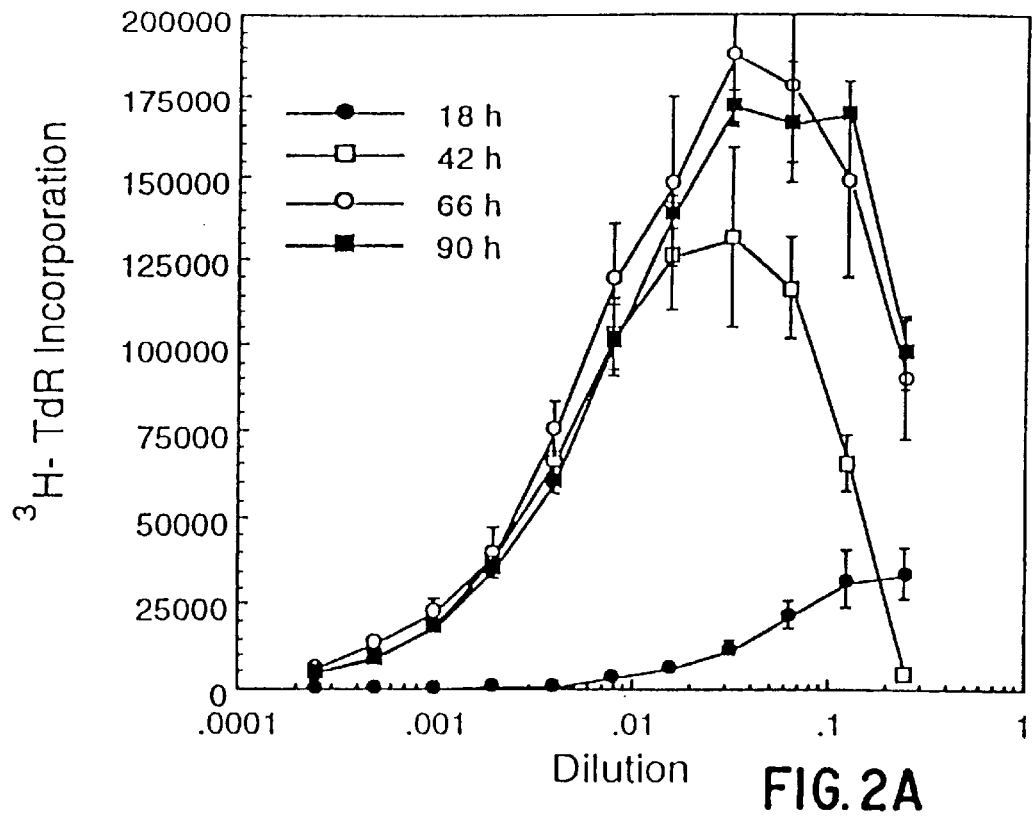

FIG. 2 Time Course of SF9 Cell Infection

A. SF9 cells were infected with a recombinant baculovirus containing mouse CD40 ligand for various times. An enriched plasma membrane fraction was prepared and each membrane preparation titrated in a B cell proliferation assay ($2 \times 10^4$ B cells/well for 72 h). Filled circles, 18 h infection; open squares, 42 h infection; open circles, 66 h infection; filled squares, 90 h infection.

B. hdmb CD40 ligand produced in A above was used to stimulate B cells in the presence of D10 sn (1/100; lymphokine-containing supernatant from 9 h stimulated D10G4.1 Th2 T cell clone, Hodgkin et al., *J. Immunology* 145:2025–2034 (1990)). Symbols as in FIG. 1A.

Figure 3:
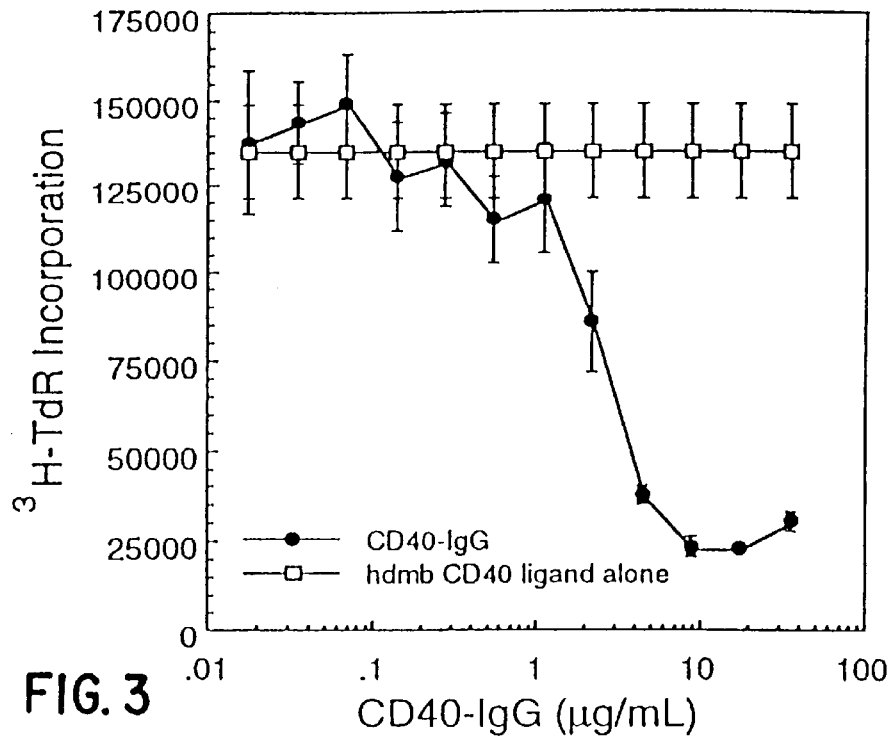

FIG. 3 Specificity of B Cell Proliferation Induced by hdmb CD40 Ligand

B cells ($2 \times 10^4$/well) were stimulated with a constant amount of hdmb CD40 ligand (1/200). Filled circles, CD40-IgG included (35 µg/ml at the highest concentration); open squares, no CD40-IgG.

Figure 4:
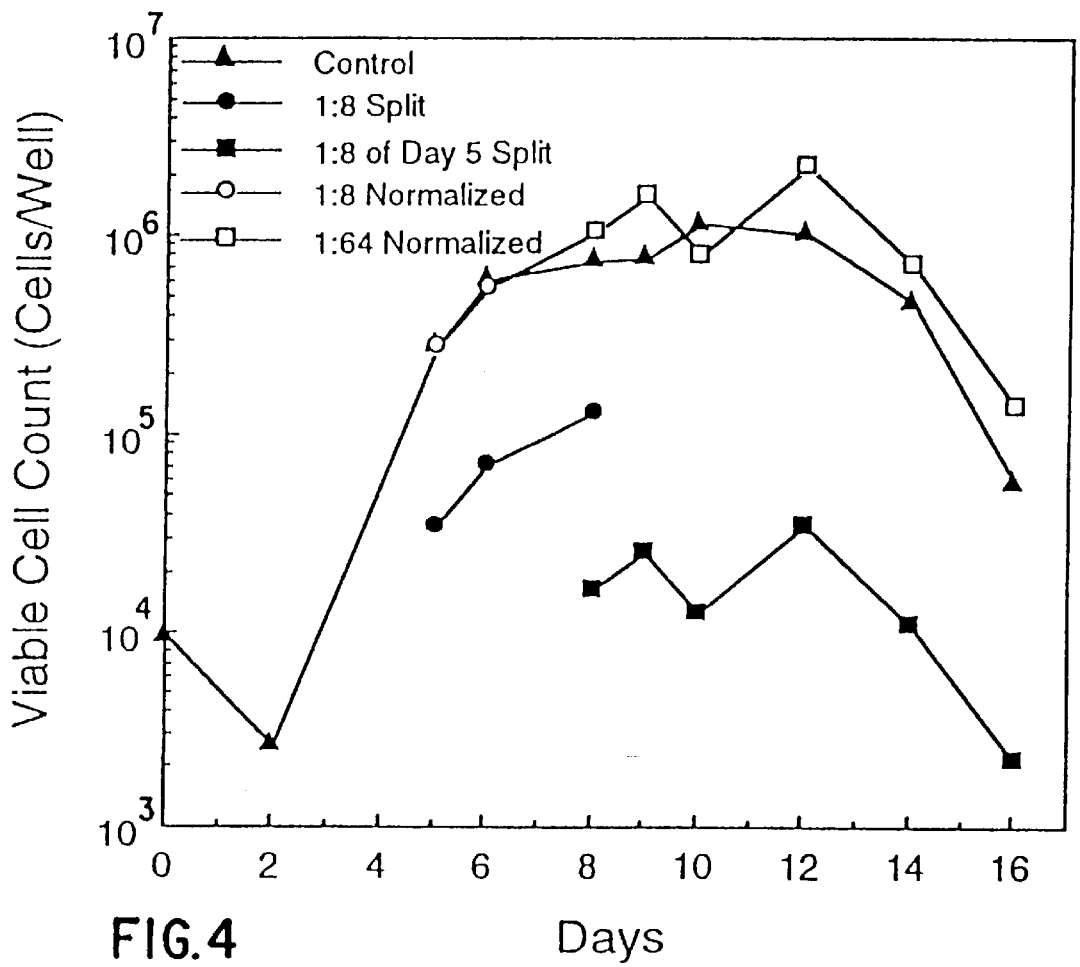

FIG. 4 Density Plating Effects on B Cells Proliferation

B cells were placed into 96 well plates ($1 \times 10^4$/well) with hdmb CD40 ligand (1/80) and D10 sn (1/100). Cells were counted and the media replaced every 48 h. At days 5 and 8 the cells were resuspended and split ⅛. Filled triangles, cells not split; filled circles, ⅛ split at day 5; filled squares, ⅛ split at day 8; open circles, ⅛ split multiplied by 8; open squares, second ⅛ split multiplied by 64.

Figure 5:
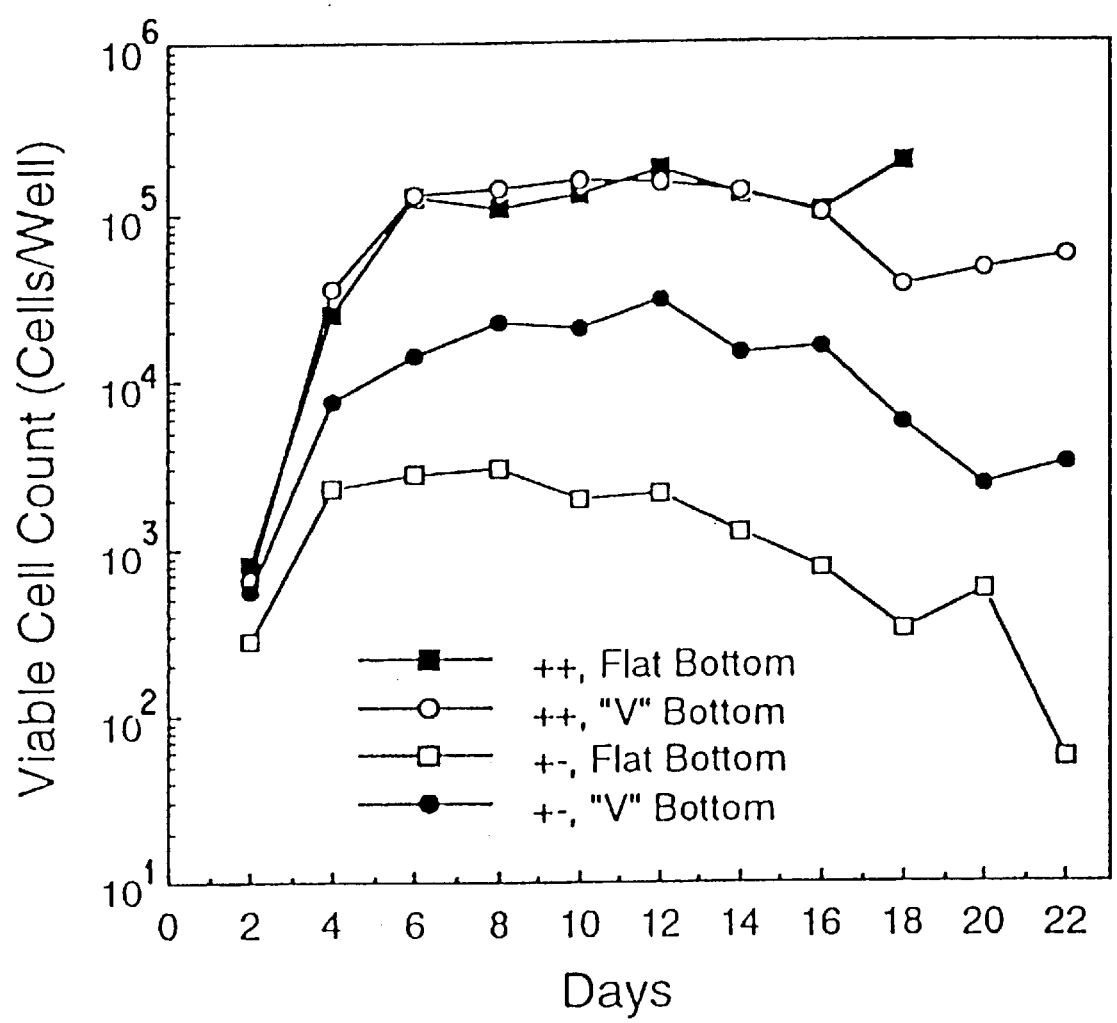

FIG. 5 Comparison of B Cell Expansion in Flat Versus "V" Bottom Wells

B cells were placed in either flat bottom or "V" bottom 96 well plates ($1 \times 10^3$/well). Cells were incubated with either hdmb CD40 ligand and D10 sn (++) or hdmb CD40 ligand membranes only (+−). Cells were counted and medium was removed and replaced every 48 h. Filled squares, hdmb CD40 ligand and D10 sn in flat bottom plate; open circles, hdmb CD40 ligand and D10 sn in "V" bottom plate; open squares, hdmb CD40 ligand in flat bottom plate; filled circles, CD40 ligand in "V" bottom plate.

FIG. 6 Growth and Antibody Secretion of B Cells Stimulated with hdmb CD40 ligand and D10 sn A. B cells were placed into 96 well "V" bottom plates ($1 \times 10^3$ cells/well) with hdmb CD40 ligand (1/300) and D10 sn (1/100). Every 48 h cells were removed and counted. Open squares, total number of viable cells; filled circles, fraction of cells which were viable.

B. Medium from replicate wells was removed for measuring antibody concentration by quantitative ELISA. Filled circles, IgM; filled squares, IgG1; filled triangles, IgE. Cumulative antibody concentrations are provided in ng/ml.

FIG. 7 Growth and Antibody Secretion of B Cells Stimulated With hdmb CD40 Ligand and D10 sn With Medium Replacement A. B cells were placed into 96 well "V" bottom plates ($1 \times 10^3$ cells/well) with hdmb CD40 ligand (1/300) and D10 sn (1/100). Every 48 h cells were removed and counted; old medium was removed and replaced with fresh medium. Open squares, total number of viable cells; filled circles, fraction of cells which were viable.

B. Medium from replicate wells was removed for measuring antibody concentration by quantitative ELISA. Filled circles, IgM; filled squares, IgG1; filled triangles, IgE. Cumulative antibody concentrations are provided in ng/ml.

Figure 8A:
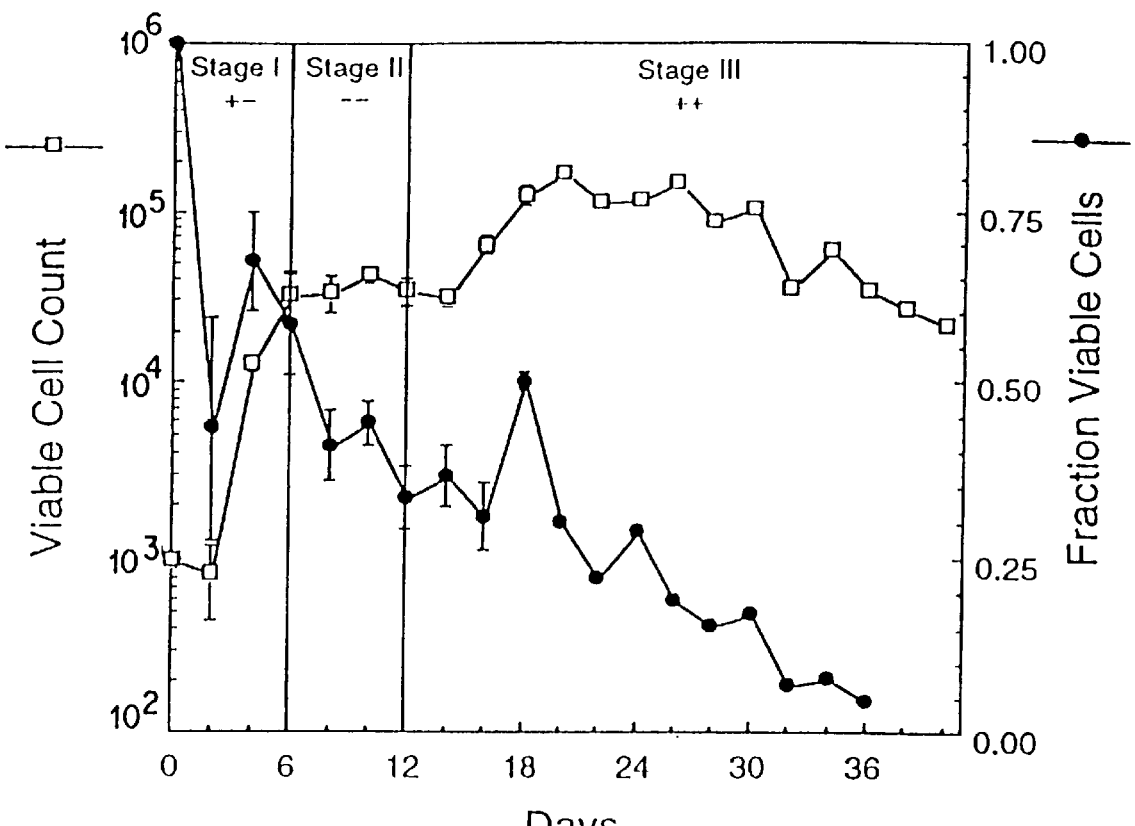
Figure 8B:
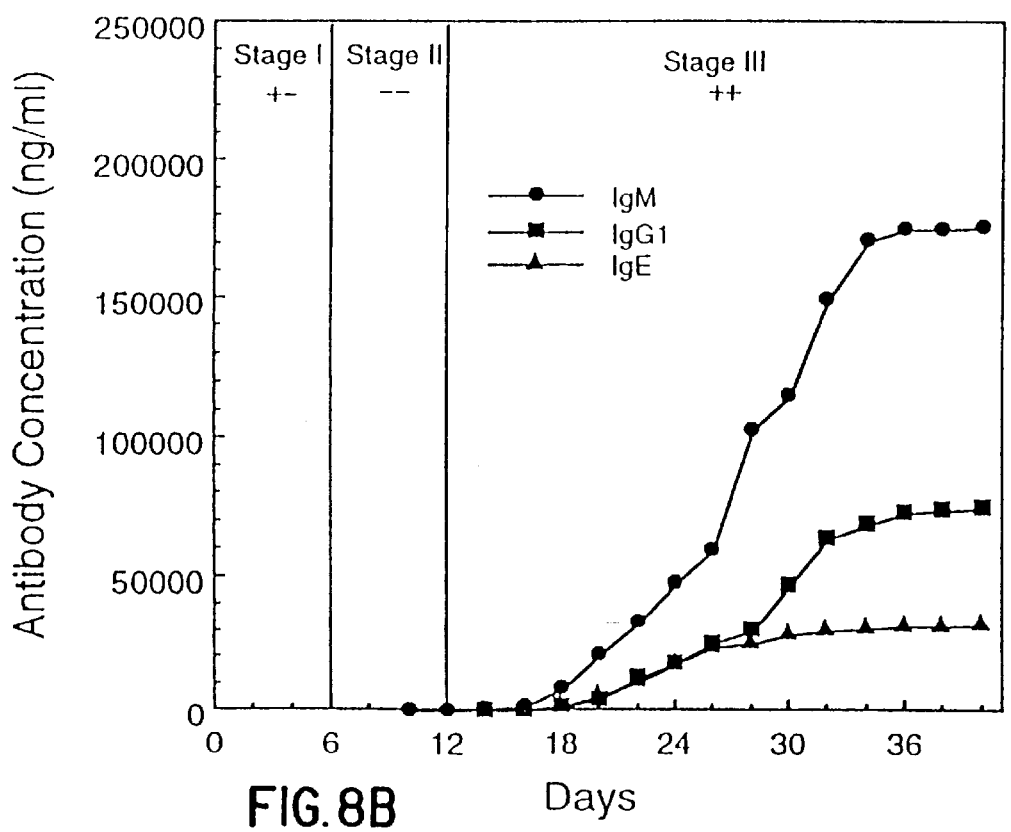

FIG. 8 Growth and Antibody Secretion of B Cells Restimulated with hdmb CD40 ligand and D10 sn With Medium Replacement A. B cells were placed into 96 well "V" bottom plates ($1 \times 10^3$ cells/well) with CD40 ligand (1/300) and D10 sn (1/100). Every 48 h cells were removed and counted; old medium was removed and replaced with fresh medium; +−, medium contained hdmb CD40 ligand; −−, medium contained no additions; ++, medium contained hdmb CD40 ligand and D10 sn. Open squares, total number of viable cells; filled circles, fraction of cells which were viable.

B. Medium for replicate wells was removed for measuring antibody concentration by quantitative ELISA. Filled circles, IgM; filled squares, IgG1; filled triangles, IgE. Cumulative antibody concentrations are provided in ng/ml.

Figure 9:
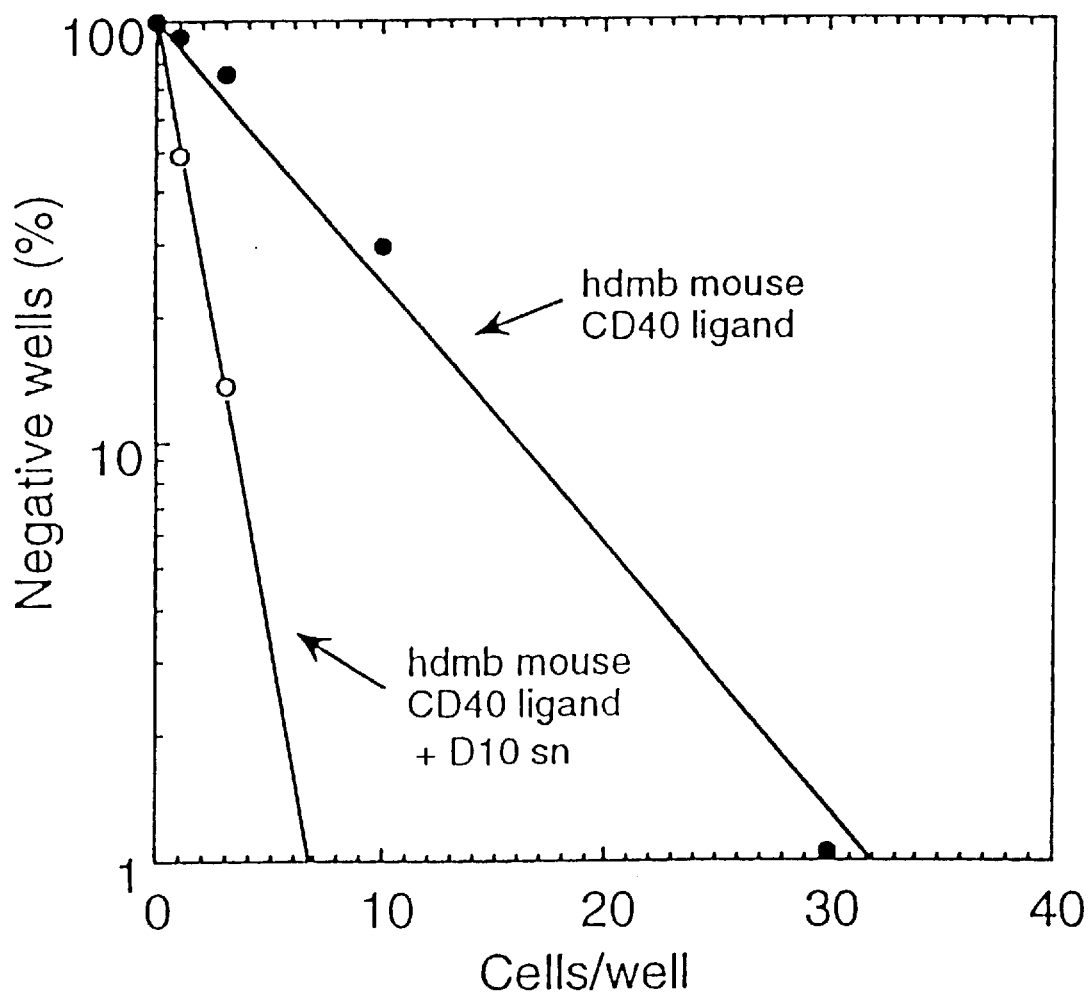

FIG. 9 Frequency of B Cells Responding to hdmb CD40 Ligand

B cells were plated at 1, 3, 10, and 30 cells/well in 96 well "V" bottom plates with either hdmb CD40 ligand (1/300) or hdmb CD40 ligand (1/300) and D10 sn (1/100). After 6 days, the cells were resuspended, transferred to flat bottom plates, and scored for the presence of viable cells ($\geq$ cells/well).

Figure 10:
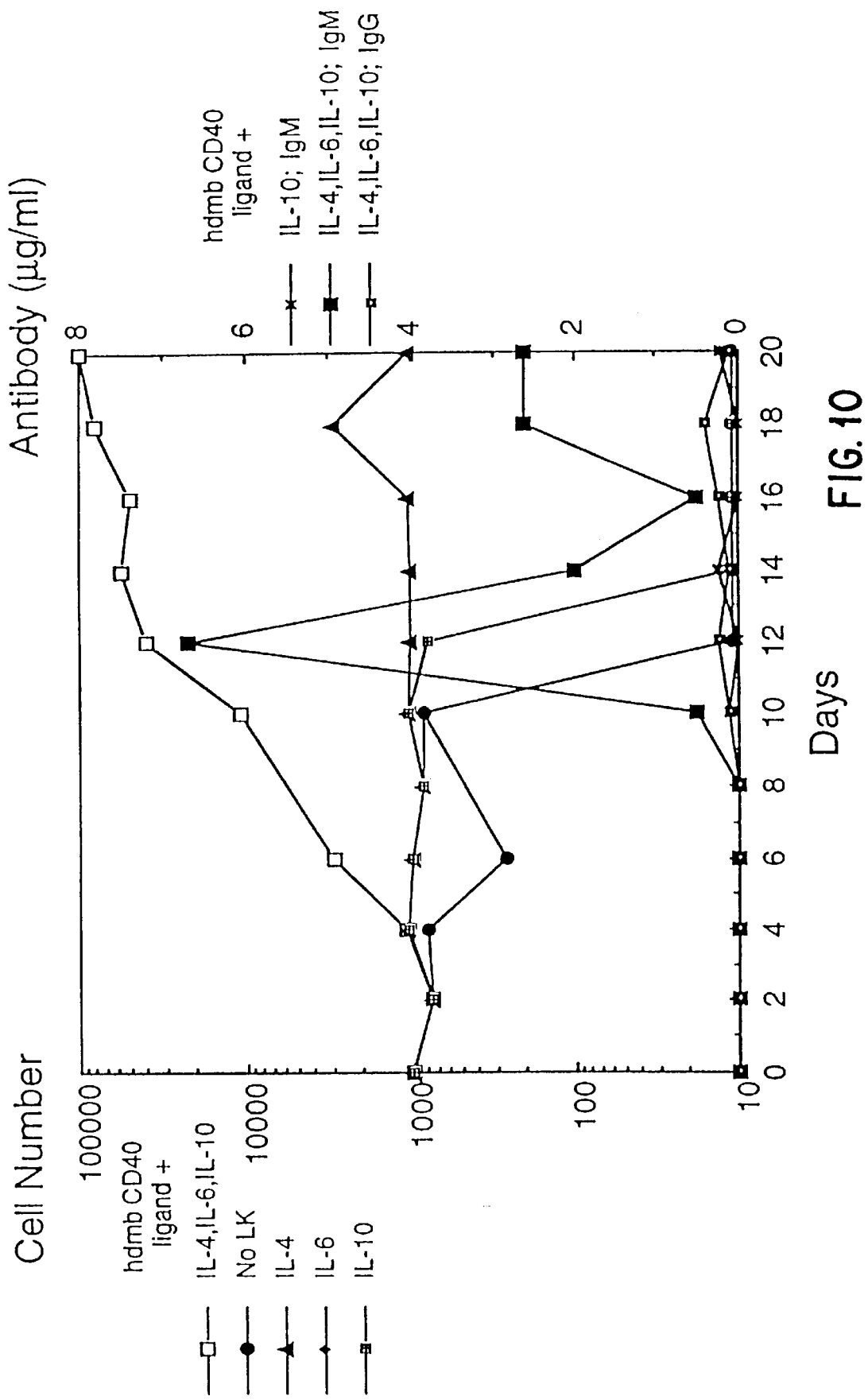

FIG. 10 Proliferation of Human B Cells

Human B cells were incubated in V-bottom wells as described in FIG. 7 with or without addition of recombinant human IL-4, IL-6, or IL-10 as indicated.

Figure 11:
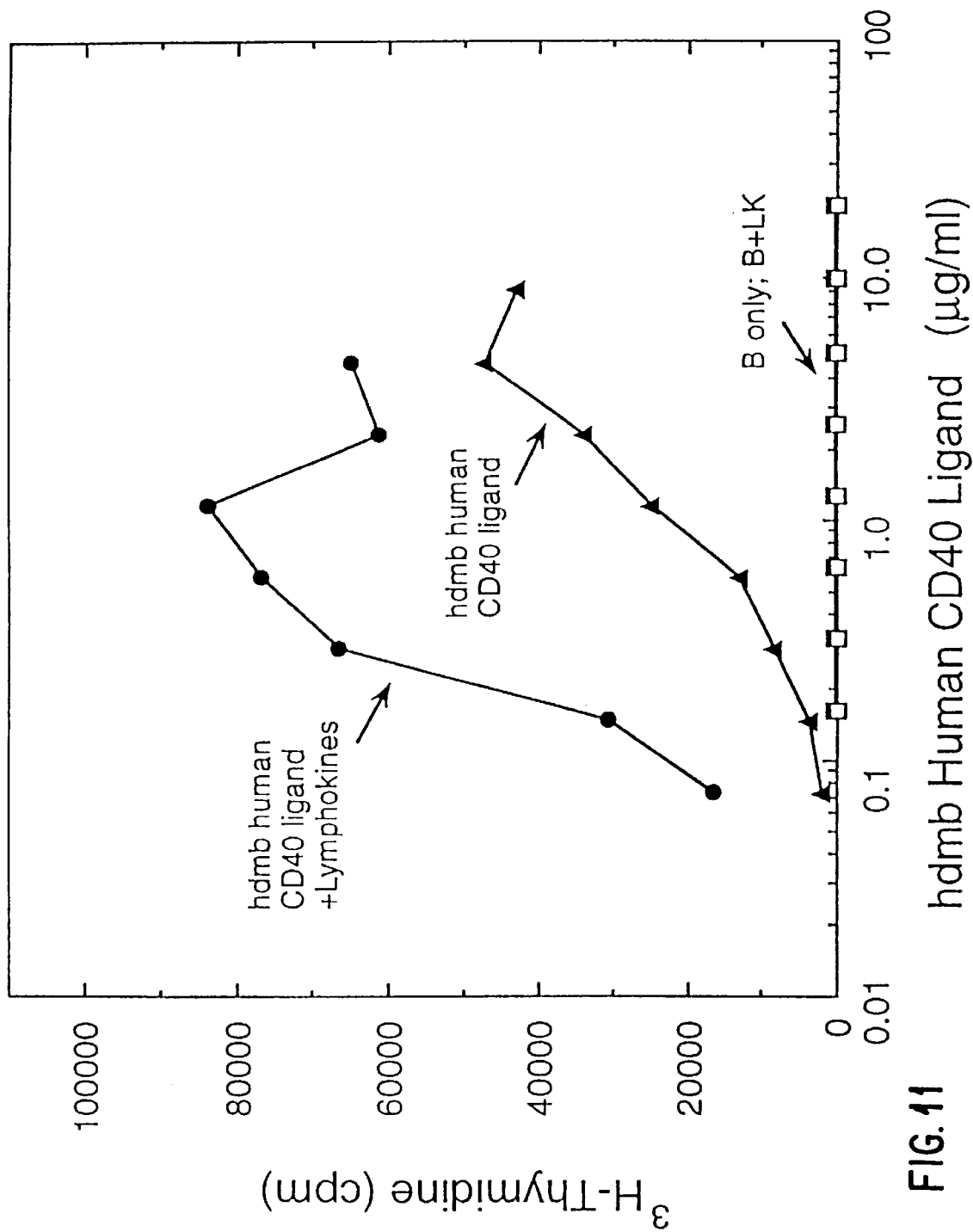

FIG. 11 Human CD40 ligand in insect cell membranes stimulates efficient human B cell proliferation.

Purified human peripheral blood B cells (7,000/well) were incubated in BCM (100 µl) with various concentrations of human hdmb CD40 ligand in the form of plasma membranes purified from SF9 cells infected with a human CD40 ligand-containing recombinant baculovirus (hereinafter hdmb human CD40 ligand). (squares), B cells in the absence of membranes; (triangles), hdmb human CD40 ligand; (circles), hdmb human CD40 ligand and a mixture of recombinant human lymphokines (IL-1α, IL-2, IL-4, IL-6, IL-10, and IL-11). $^3$H-Thymidine (1 µCi/well) was added during the last 6 h of the 96 h culture period. Each point is the mean of duplicate wells.

FIG. 12 Clonal frequency of human B cell growth and differentiation.

Purified human peripheral blood B cells were plated at 1, 3, 10, and 30 cells/well in V-bottom 96-well plates in the presence of hdmb human CD40 ligand (1 µg/ml) and a mixture of recombinant IL1α, IL-2, IL-4, IL-6, IL-10, and IL-11 (150 µl total). On days 4, 8, and 11, old medium was removed and replaced with fresh medium containing hdmb human CD40 ligand and lymphokines. (A) Wells containing viable cells (≧4 cells/well) were scored on day 14 after resuspending cells and transferring to flat bottom 96 well plates. Dashed lines indicate the number of B cells/well where 37% of the cultures were negative for growth. According to Poisson's distribution, at this cell number each well would contain one growing cell. (B) Media harvested from plates on day 11 were assayed for the presence of human IgM and human IgG by separate ELISA assays. Number of wells positive for IgG and IgM were combined for scoring. Dashed lined indicate the number of B cells/well where 37% of the cultures were negative for antibody production.

Figure 13:
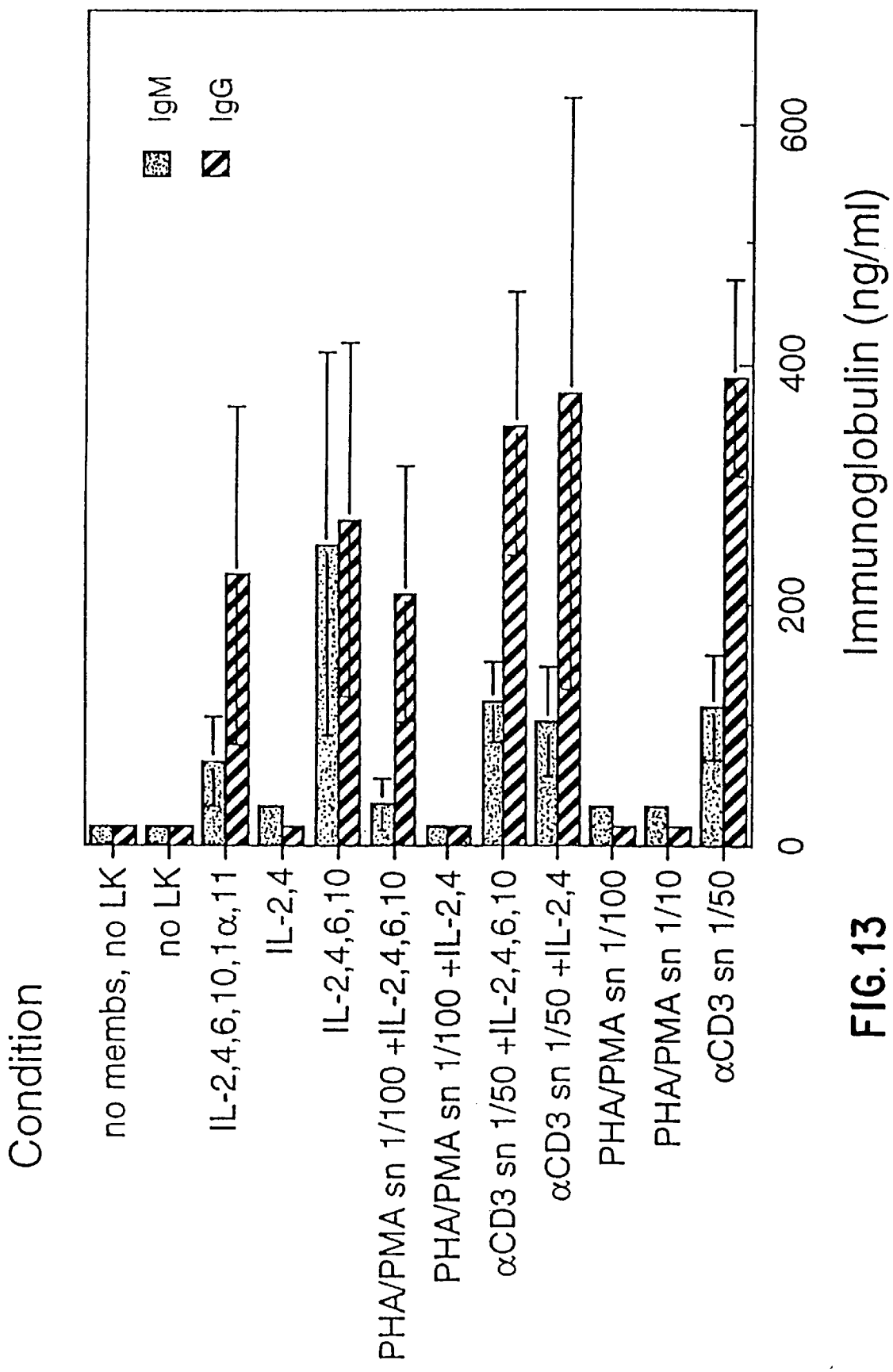

FIG. 13 IgM and IgG secretion by human B cells stimulated with different lymphokine combinations.

Human peripheral blood B cells (500/well) were incubated in V-bottom 96 well plates with hdmb human CD40 ligand (1 μg/ml) in the presence of the indicated lymphokines in 150 μl BCM for 14 days. Culture supernatants were harvested and levels of IgM and IgG determined by ELISA. Each point is the mean±S. E. of 4 replicate wells. Lymphokine concentrations were supplied as described in Example 3, Materials and Methods. PHA/PMA sn, culture supernatant from PHA and PMA-activated peripheral blood T cells; αCD3 sn, culture supernatant from anti-CD3 activated peripheral blood T cells. Final concentrations of human T cell supernatants are indicated.

Figure 14:
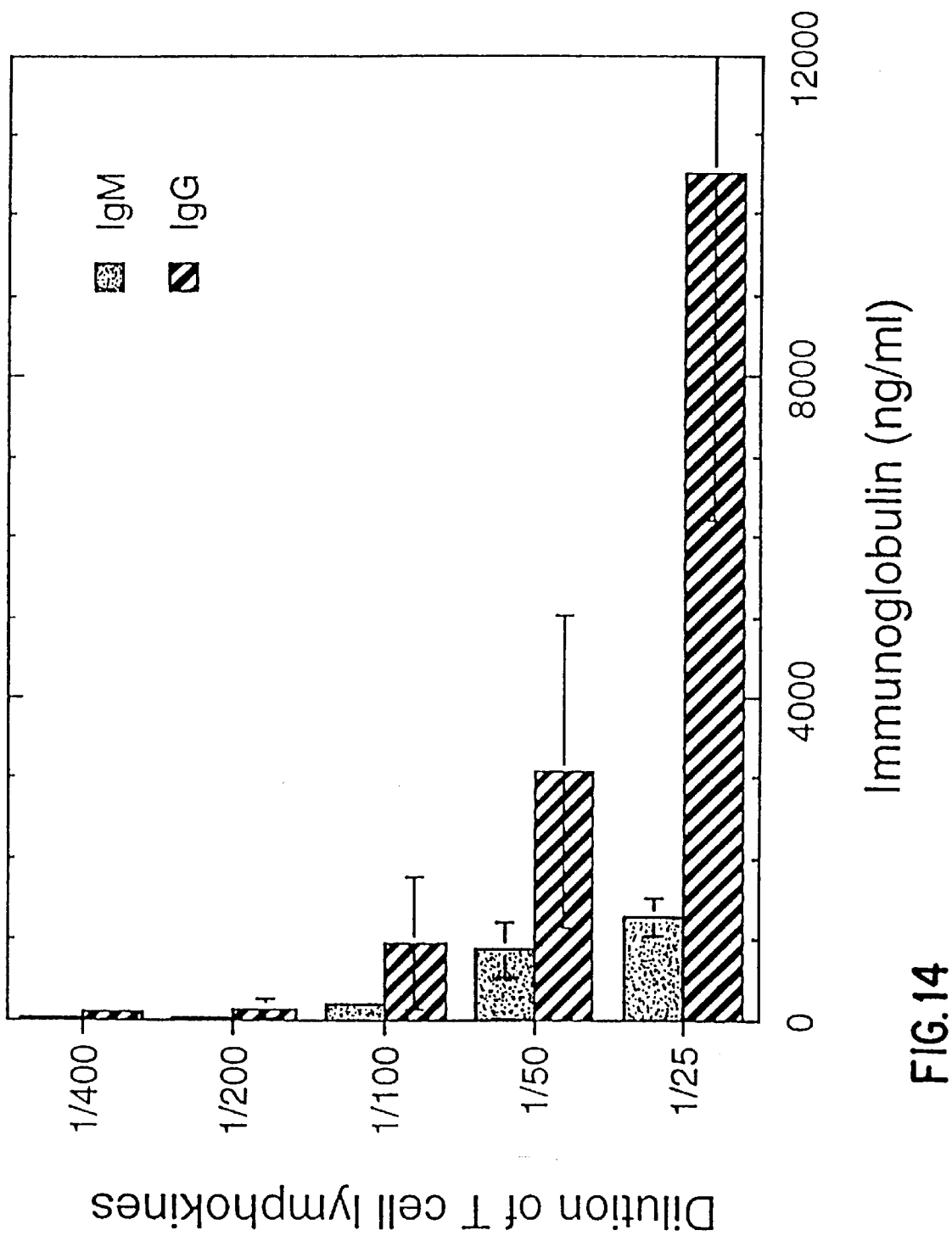

FIG. 14 Cytokine-dependent human B cell differentiation.

Human peripheral blood B cells (500/well) were incubated in V-bottom 96 well plates with hdmb human CD40 ligand (1 μg/ml) in the presence of various dilutions of supernatant from anti-CD3 activated peripheral blood T cells in 150 μl BCM. On day 23, medium was removed and the levels of IgM (dotted bars) and IgG (cross-hatched bars) determined by ELISA. Each point is the mean±S.E. of four replicate wells.

Figure 15:
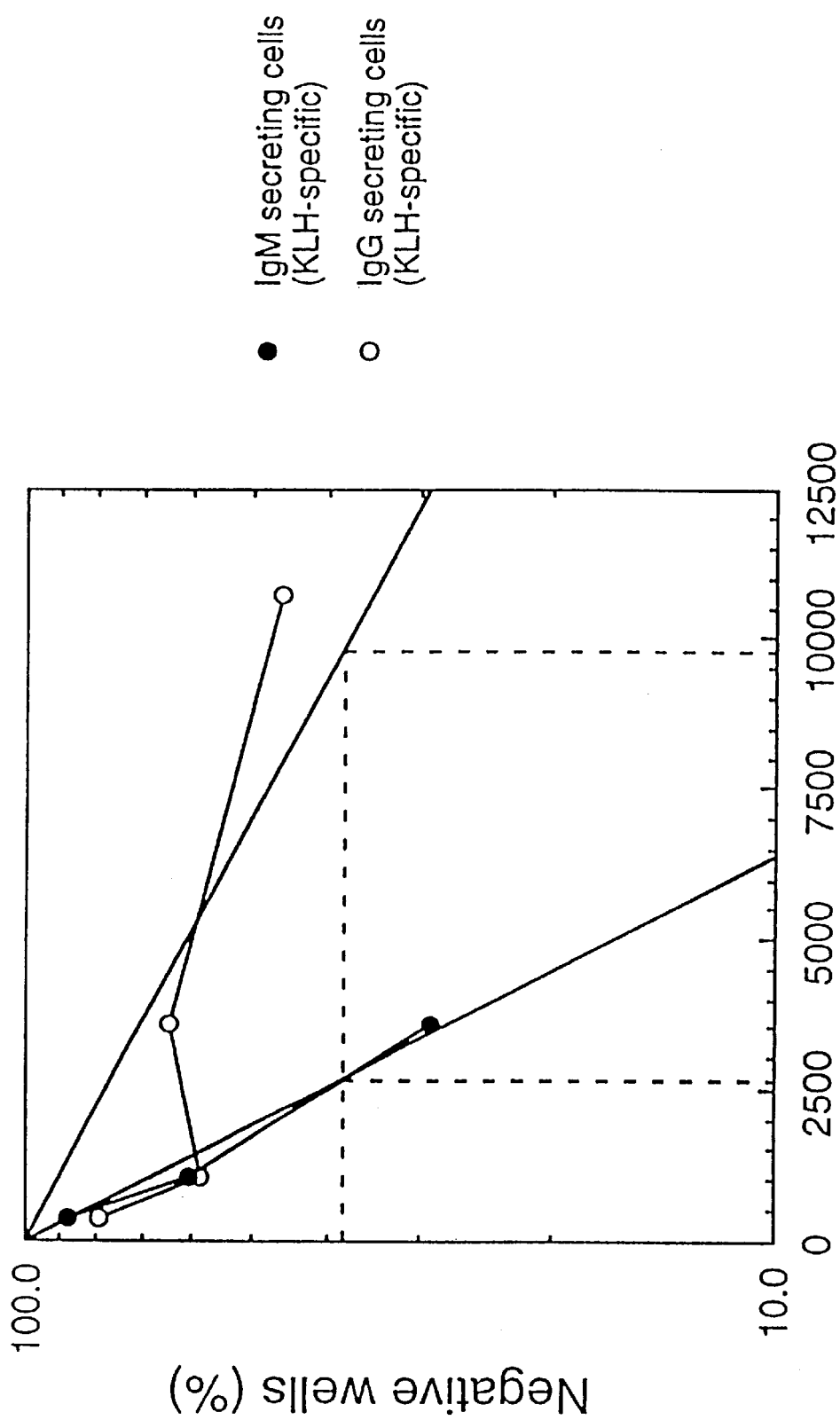

FIG. 15 Clonal frequency of antigen-specific mouse B cells in unprimed spleen.

Dense splenic mouse B cells were plated at 1000, 3000, 10,000, and 30,000 cells/well in V-bottom 96-well plates in the presence of mouse hdmb human CD40 ligand (0.1 μg/ml) and D10 supernatant (1/100) in 150 μl BCM. On days 5, 8, and 12, old medium was removed and replaced with fresh medium containing Sf9$^{CD40L}$ and lymphokines. On day 14 wells were assayed for the presence of KLH-specific antibody secreting cells by ELISPOT as described in Example 3, Materials and Methods. Each well on the original plates was divided between two identical ELISPOT plates; one of the duplicate plates was developed for IgM and the other was developed for IgG. Wells were scored positive for specific IgM-secreting cells (≧3 spots/well) or specific IgG-secreting cells (≧4 spots/well) under a dissecting microscope. Dashed lines indicate the number of B cells/well where 37% of the cultures were negative for antigen-specific antibody production.

DETAILED DESCRIPTION OF THE PREFERRED EMBODIMENT

The present invention is based on the observation that high density, membrane bound CD40 ligand (hereinafter hdmb CD40 ligand), can induce high level proliferation of B cells in culture. In addition, it has been found that by varying the types and concentration of cytokines and/or contact cells which are present during proliferation, proliferating B cells can be induced to differentiate into antibody producing cells. Lastly, it has been observed that proliferation and differentiation in the presence of an antigen preferentially proliferates or selects differentiating B cells to produce antibodies specific to the antigen supplied.

Based on the above observations, one embodiment of the present invention provides methods for proliferating B cells which comprises the step of culturing one or more B cells in the presence of hdmb CD40 ligand.

As used herein, proliferation is defined as the process of expanding (increasing) the number of B cells from a starting of one or more cells to a greater number of cells. In the examples that follow, evidence for proliferation of 250-fold (eight rounds of division over six days) is presented. The degree and amount of proliferation obtained using the present methods, will vary depending on the type and nature of the initial B cells used as well as the culture conditions employed. However, so long as the number of live B cells present in the culture increases as a result of division or increased survival of the dividing population, the B cells are said to be proliferating (see FIGS. 2, 6, 7, 8 and 10).

As used herein, B cells, or a B cell population, refers to one or more cells which are derived from a primary explant containing B cells or a culture derived therefrom (for a definition of B cells and B cell populations, see Parker, *Annu. Rev. Immunol.* 11:331–360 (1993)). The preferred B cells for use in the present invention are classified as "small dense B cells." As described in the examples which follow, small dense B cells can be purified from the spleens, peripheral blood, bone marrow or cells isolated from lymphoid organs of a mammal using techniques known in the art, for example, see Hodgkin et al., *J. Immunology* 145:2025–2034 (1990), Clark et al. *J. Immunology* 148:3327–3335 (1992), Thomas et al. *J. Immunology* 150:821–834 (1993), Freudenthal et al. *PNAS USA* 87:7698 (1990).

The initial starting population of B cells can consist of a primary explant of isolated small dense B cells (approximately 1,000 cells), be a primary explant of singly isolated B cells, be obtained from existing B cell cultures produced by the methods herein described or be isolated peripheral blood cells, bone marrow cells, and cells derived from lymphoid organs. A skilled artisan will know how to vary the condition of culture depending on the source and size of the starting population using known parameters (see FIG. 4 and 11).

The procedures of the present invention can be applied to B cells isolated from any mammal. The examples below provide evidence of the ability of hdmb CD40-ligand to proliferate both mouse and human B cells (FIGS. 2, 7 and 9–12).

As used herein, "culturing" refers to the set of procedures used in vitro where a population of cells (or a single cell) is incubated under conditions which have been shown to support the growth or viability of the cells in vitro. The art recognizes a wide number of formats, medias, temperature ranges, gas concentrations etc. which need to be defined in a culture system. The parameters will vary based on the format selected and the specific needs of the individual who practices the methods herein disclosed. However, it is recognized that the determination of culture parameters is routine in nature.

Any one of the wide variety of formats, including, but not limited to, hollow fiber technology and immobilization on solid support or culture flasks, can be adapted for use in the currently disclosed methods since such formats have been employed successfully in the culture of other mammalian cell types. In the examples that follow, B cells were incubated in V bottom or flat bottom 96 well microtiter plates with sterile platelids (FIG. 5, 10, and 11). During culturing, the plates were incubated in 5.5% $CO_2$ at 37° C. These procedures were used to culture small dense B cell masses (of approximately 1,000 cells) as well as 1, 3, and 10 cells per well to grow selected B cell clones. These procedures were selected only as an example of the wide variety of formats and conditions which can be employed.

In addition to a wide variety of formats, any of the currently known mammalian cell culturing medias can be employed in the presently claimed methods. A skilled artisan can determine the suitability of a particular media and format/media combination for use in the present claimed methods using known procedures. In the examples that follow, B cell media (BCM) which consists of 10% fetal calf serum (HyClone characterized), 10 mM hepes pH 7.3, L-glutamine, penicillin/streptomycin, non-essential amino acids, sodium pyruvate, $5 \times 10^{-5}$M mercaptoethanol in RPMI 1640 media and 100× supplements from Gibco was used. Detailed reviews of other known formats and culturing conditions used in mammalian cell culturing are known in the art.

The presently claimed methods are based largely on the use of hdmb CD40 ligand. As used herein, "CD40 ligand" refers to any protein which possess substantial similarity to one of the known amino acid sequences of CD40 ligand and possess CD40 ligand activity (for a review of the amino acid sequence and nucleic acid sequence encoding CD40 ligands see Armitage et al., *Nature* 357:80–82 (1992); Hollenbaugh et al., *EMBO J.* 11:4313–4321 (1992)). As used herein, two proteins are said to have substantial similarity in the amino acid sequence when an active domain or a region involved in receptor binding contains 80% or greater amino acid sequence homology. The preferred CD40 ligands of the present invention are human CD40 ligand and mouse CD40 ligand.

The CD40 ligand of the present invention can be isolated from cells which naturally express CD40 ligand, or can be purified from cells which have been altered to express CD40 ligand. For a detailed review of the application of recombinant procedures to the production of CD40 ligands, see, Armitage, *Nature* 357:80–82 (1992) and Hollenbaugh et al., *EMBO J.* 11:4313–4321 (1992), as well as the examples that follow.

The CD40 ligand which is used in the present method is a membrane bound form of CD40 ligand. As used herein, "membrane bound CD40 ligand" refers to CD40 ligand which is attached to a lipid or plasma membrane. The attachment of CD40 ligand to a membrane can be accomplished in several fashions. For example, CD40 ligand can be attached to a membrane using the natural transmembrane domain of CD40 ligand since CD40 ligand is a naturally occurring transmembrane protein. By isolating naturally occurring CD40 ligand from cells which naturally express or which have been altered to express CD40 ligand, the CD40 ligand which is obtained is the membrane bound form. The enriched or purified CD40 ligand is obtained from cells as a membrane fraction or can be isolated as a solubilized molecule and reconstituted with lipids to form an artificial membrane.

Alternatively, CD40 ligand or soluble derivatives of CD40 ligand, can be attached to a plasma membrane through the use of an appropriate membrane protein linker and a protein cross-linking agent or a GPI linkage. In general, the concept of and procedures for anchoring a protein to a membrane are well known in the art. For example, a known protein cross linking agent can be used to cross-link CD40 ligand to a lipid membrane which contains integral membrane proteins with exposed activatable residues. A skilled artisan can readily adapt any one of the variety of the known membrane anchoring techniques in order to obtain membrane bound CD40 ligand.

As used herein, "high density" refers to membranes which contain CD40 ligand at least at a density 10 fold greater than that found on cells which naturally express CD40 ligand, and more preferably 100 fold greater. It has been observed that previous attempts at expressing CD40 ligand in a recombinant host have resulted in the production of CD40 ligand at densities similar to those found on cells which naturally express CD40 ligands.

A variety of procedures can be used to determine the "density" of CD40 ligand. These include but are not limited to fluorescence microscopy, fluorescent activated cell analysis, receptor/ligand binding assay, and immunoreactivity. (For example, see Castle et al., *J. Immunol.* 151:1777–1788 (1993).)

As discussed above, a variety of procedures can be used to obtain high density membrane bound CD40 ligand. The preferred method of the present invention is to express CD40 ligand in cultured insect cells infected with a modified baculoviral vector. It has been found that CD40 ligand can readily be expressed in insect cell cultures as a high density, membrane bound form. A skilled artisan can readily adapt known baculoviral expression systems to produce CD40 ligand in a high density membrane bound form. The examples below demonstrate the use of cultured SF9 cells to produce hdmb CD40 ligand for use in the presently claimed methods (see FIG. 2).

Previous attempts at proliferating B cells in the presence of naturally isolated membrane bound CD40 ligand, membrane bound CD40 ligand produced from transfected animal cells, or recombinantly expressed soluble derivatives of CD40 ligand has yielded poor results. Proliferation tends to be moderate, ending after 1–4 rounds of replication. The present invention provides improvements over the use of previous forms of CD40 ligand in that proliferation responses have been demonstrated to be as great as 250-fold. The presence of lymphokines when hdmb CD40 ligand is used results in the differentiation of the proliferating B cells into antibody producing cells.

The present method can be used in a single step proliferation procedure or in a multi-step procedure. In a multistep procedure, hdmb CD40 ligand is included in the culture media during the initial phases of culturing. The presence of hdmb CD40 ligand is maintained until the rate of proliferation decreases. The cells are then rested by culturing under conditions where hdmb CD40 ligand is not present. After resting the cells, the cells can be restimulated to continue proliferation by adding the hdmb CD40 ligand and cytokines back to the culture (see FIG. 8). The underlying mechanism for a resting stage following a proliferation stage using hdmb CD40 ligand is unknown. However, it was found that many activated B cell populations require such a resting phase after the rate of initial proliferation has decreased. A skilled artisan can readily monitor B cell proliferation and remove the hdmb CD40 ligand from the culturing media when the rate of the proliferation of the B cells declines.

A variety of procedures can be used to monitor the proliferation of B cells. These include, but are not limited to, measuring the incorporation of a labeled compound, such as tritiated thymidine, or by direct cell counting techniques. Both of these procedures are described in more detail in the examples that follow.

Specific time points for a multi-step proliferation procedure can readily be determined by a skilled artisan using the procedures described above. In the following examples, the procedure used was to culture B cells (an isolated small dense population) in the presence of hdmb CD40 ligand for six days (proliferation stage). After six days of culturing, the hdmb CD40 ligand was removed from the culture media and the cells are fed for six more days (resting stage). After the sixth day of the resting phase in which the hdmb CD40 ligand was not present, the cells were recultured in the presence of hdmb CD40 ligand and appropriate cytokines (reproliferation stage).

A further embodiment of the present invention is based on the observation that cytokines, extracts from selected cells, agents which cross-link surface receptors and Ig molecules, and/or selected feeder cell populations, when added to B cells which are proliferating or have been proliferated using the above described methods, stimulate the B cells to differentiate into antibody producing cells. Based on this observation, the present invention provides methods for differentiating proliferating B cells which comprise the step of culturing B cells in the presence of hdmb CD40 ligand and a cytokine, feeder cells or extract thereof.

As used herein, cytokines refer to the class of molecules which have been demonstrated to have cell differentiating and/or growth promoting activity. Cytokines can be identified and added to the culture media in highly purified form, for example as purified interleukin-1, IL-2, IL-4, INF-α, etc., or can be supplied as supernates or extracts obtained from stimulated cells which produce the cytokines. In the present invention, Th2 lymphokines were used to differentiate mouse splenic B-cells while either lymphokines secreted by anti-CD3-activated T cells or a combination of recombinant IL-2, IL-4, IL-6, and IL-10 supported differentiation of hdmb CD40L-stimulated human peripheral blood B cells. Specifically, for mouse B-cells, the Th2 clone D10.G4.1 was stimulated for nine hours with concanavalin A and the culture supernates were mannose/agarose absorbed, ultracentrifuged at 100,000 g for 30 minutes, sterile filtered, and stored at −80° C. prior to use (Th2 SN or Th2 supernate) (see Hodgkin et al., *J. Immunology* 145:2025–2034 (1990)). The isolated Th2 supernate was then used to stimulate the differentiation of the proliferating mouse B cells.

For differentiating human peripheral blood B-cells, a lymphokine containing supernate was prepared as follows. Peripheral blood mononuclear cells obtained after centrifugation over Ficoll-Hypaque were panned sequentially on plates coated overnight with anti-CD14 (5 µg/ml), anti-CD14 and anti-CD19 (2.5 µg/ml each), and anti-CD8 (5 µg/ml). Panning was in Hank's balanced salt solution, 5% FBS, 10 mM HEPES, pH 7.3 at 4° C. for 1 h. Nonadherent cells were washed and resuspended at $4\times10^6$ cells/ml in warm BCM [RPMI 1640 supplemented with 10% FBS, 10 mM HEPES (pH 7.3), 2 mM L-glutamine (GIBCO, Grand Island, N.Y.), 0.1 mM nonessential amino acids (GIBCO), 1 mM sodium pyruvate, $5\times10^{-5}$M 2-mercaptoethanol, and 100 U/ml each penicillin and streptomycin (GIBCO)]. For anti-CD3 stimulation, cells were placed on tissue culture dishes coated with 4 µg/ml anti-CD3 for 48 h at 37° C. For stimulation with PHA/PMA, cells were incubated with 2.5 µg/ml PHA and 10 ng/ml PMA for 2 h at 37° C., washed and incubated in fresh warm BCM for 46 h at 37° C. After removal of cells by low speed centrifugation, supernatants were centrifuged at 100,000×g, filtered through a 0.2 µM membrane, and stored in aliquots at −80° C.

Additionally, cytokines produced by other cell types, including dendritic cells, follicular dendritic cells, and other antigen presenting cells, in the presence or absence of specific antigen, can be included in the cultures as stimuli. In addition to the Th2 and anti-CD3 stimulated supernate which was used in the examples, a skilled artisan can readily utilize any known cytokine in the present differentiation procedures.

In addition to specific cytokines or cytokine containing supernatants, feeder layers, cellular extracts obtained from other cells involved in B cell differentiation, and/or agents which cross link B cell surface molecules can be added to proliferating B cells to stimulate differentiation. For example, B cells are known to interact with follicular dendritic cells during maturation. Membrane extracts, culture supernates or purified molecules derived from follicular dendritic cells (obtained in the same manner as that described for Th2 supernates), or a feeder layer of follicular dendritic cells can be used to stimulate the differentiation of the proliferating B cells or augment differentiation which is stimulated through the use of other cytokines as described above. Further, agents such as antibodies, which cross link surface receptors signal the differentiation of the proliferated and proliferating B cells (in some cases, these agents will induce somatic hypermutation in the CDRs of the variable regions of the antibody encoding DNA within the B cell). Anti-IgD or anti-IgM antibodies which cross link membrane bound Ig molecules on the B cell have been shown to stimulate class switching for the secreted antibody (for example, leading to the production of high levels of IgA antibodies).

The cytokines, cell extracts/supernatants, or feeder cells used to stimulate differentiation can be added to the B cells at any one of a variety of time points during culturing. For example, cytokines can be added at the start of culturing. Using such a procedure, antibody production normally begins around day 8 to 10 (FIGS. 6, 7, 10 and 13). Alternatively, cytokines can be added during the resting or reproliferation phase if a multi-step process is used. The advantage of a multi-step approach is that it allows an initial small B cell population be to proliferated and/or selected prior to differentiation.

A variety of procedures can be used to monitor the differentiation of B cells. Such procedures include, but are not limited to, examining the morphological characteristics of the proliferating cells, assays which determine the presence of antibody protein, assays for cell surface markers, and methods which assay for the presence of nucleic acid sequences which encode antibodies (FIGS. 6, 7, 10, 13 and 14). A skilled artisan can readily adapt any of these procedures to monitor the differentiation of proliferating B cells which are obtained using the herein disclosed methods.

During differentiation, it may be preferable to clone out selected individuals or subpopulations of the proliferating B cells in order to obtain clonal cell lines. Such procedures are most readily accomplished using cell plating techniques known in the art (see FIGS. 9, 12, and 15). A skilled artisan can readily apply such cloning procedures to the proliferating and differentiating B cells produced by the methods herein disclosed.

A third embodiment of the present invention is based on the observation that the differentiation of proliferating B cells can be partially controlled by including an antigen in the culture media. Specifically, the percentage of B cells which produce an antibody selective for a specific antigen can be increased by adding an antigen to the culture media during the proliferation phase, the differentiation phase, or the reproliferation phase of the herein described methods.

As used herein, an antigen is a compound which has been shown, or can be shown, to stimulate an antibody response when administered to a mammalian host. Antigens come in a variety of forms and include, but are not limited to, proteins, carbohydrates, synthetic compounds, and vitamin derivatives. A skilled artisan can readily apply known procedures to determine the antigenicity of a particular compound.

In one application of the above method, an antigen is added to the culture media when the cytokine (or other differentiating agent) is present. For example, in procedures where the cytokine is added during the initial proliferation, the antigen is supplied at that stage of incubation. In procedures where the cytokine is added after the initial proliferation stage, the antigen is added at that stage. Further, a skilled artisan can readily use known procedures to increase the antigenicity of an antigen as well as to insure that the antigen comes in contact with the proliferating and differentiating B cells. Such procedures may include coupling the antigen to a protein or carbohydrate carrier to increase properties such as solubility and antigenicity, or to couple the antigen to the surface of a membrane or plastic culture well to selectively adhere (pan) differentiating B-cells expressing surface antibodies to the coupled antigen.

In one example of antigen use, the antigen is coupled to the membrane containing the hdmb CD40 ligand. The coupling of an antigen to the hdmb CD40 ligand acts to preferentially target the hdmb CD40 ligand to B cells which recognize the particular antigen. In another example, the antigen or antigen/hdmb CD40 ligand is provided as a dextran co-polymer. Co-polymerization with dextran is known to increase the epitopic density of an antigen, thus increasing the number and degree of B cell contacts available.

Although antigen stimulation has been found to increase the percentage of B cells which differentiate to produce antibodies directed to the antigen, such preference is not complete throughout the entire population of proliferating B cells. Therefore, a skilled artisan will need to employ known cloning or panning procedures in order to isolate specific clonal lines of differentiated B cells which produce antibodies directed to the antigen supplied.

The above procedures for proliferation and differentiation can be used for a variety of purposes and use. A skilled artisan can readily recognize the value of being able to proliferate and obtain large numbers of B cells, and in particular, human B cells. Specifically, such procedures eliminate the need for immortalization of B cell lines to obtain usable/workable quantities of B cell-derived materials. B cell-derived materials are recognized as useful in the development of antibody based pharmaceutical compounds. Prior to Applicants' invention, research directed at human B cells was limited because of the availability of starting material. The present invention now provides supplies of expanded B cells for such endeavors.

Proliferated B cells, differentiated or not, can serve as a source of mRNA which encodes all or a portion of an antibody molecule. Because of the limited amount of antibody encoding mRNA which is produced by a B cell, and the polyclonal nature and limited clonal number of B cells found within a mammalian host, it is difficult to obtain sufficient quantities of an mRNA encoding a desired antibody from single B cells for use in recombinant antibody production techniques. By providing a method for proliferating and differentiating B cells, the present invention provides a source for starting material which a skilled artisan can use to obtain mRNA which encodes an antibody.

Further, a skilled artisan can identify B cells which react with specific antigens for further use. Prior to engaging in antibody engineering, it is preferable to determine the specificity (what antigen is recognized) of the antibody produced by a B cell or B cell clone. Although PCR procedures allow one to isolate the nucleotide sequence encoding an antibody from as few as a single cell, cell masses of at least 100 cells are required to isolate and characterize the nature of a secreted antibody. The present invention provides methods for obtaining such material.

In addition to in vitro use, CD40 ligand has been described in the literature as providing a means of proliferating and activating B cells within a mammalian host. In general, pathological conditions which result in a suppression of B cell proliferation and activation can be treated using the hdmb CD40 ligand of the present invention. By supplying a mammal with hdmb CD40 ligand, B cell populations can be proliferated within a host at a level which is much greater than that found with previously produced forms of CD40 ligand. Further, hdmb CD40 ligand can be used to proliferate and/or differentiate B-cells in vitro which can then be supplied back to the host they were removed from or another compatible host. Such a procedure allows proliferation of B cells outside the host, reducing the risk of negative effects of in vivo therapeutics.

The therapeutic effects of the agents of the present invention may be obtained by providing hdmb CD40 ligand (hereinafter the agent) to a patient by any suitable means (i.e., inhalation, intravenously, intramuscularly, subcutaneously, enterally, or parenterally). It is preferred to administer the agent of the present invention so as to achieve an effective concentration within the blood. For achieving an effective concentration within the blood, the preferred method is to administer the agent by injection. The administration may be by continuous infusion, or by single or multiple injections.

In providing a patient with hdmb CD40 ligand, the dosage of the administered agent will vary depending upon such factors as the patient's age, weight, height, sex, general medical condition, previous medical history, etc. In general, it is desirable to provide the recipient with a dosage of agent which is in the range of from about 1 pg/kg to 10 mg/kg (body weight of patient), although a lower or higher dosage may be administered.

The therapeutically effective dose can be lowered by using the present composition in combination with another agent which has immuno-stimulatory activity (such as, for example, IL-4, IL-14, a specific antigen, or an anti-immunoglobulin antibody). As used herein, two or more compounds are said to be administered "in combination" with each other when either (1) the physiological effects of each compound, or (2) the serum concentrations of each compound can be measured at the same time.

The agents of the present invention are intended to be provided to recipient subjects in an amount sufficient to increase the numbers of B cells in the host. The administration of the agent(s) of the invention may be for either a "prophylactic" or "therapeutic" purpose. When provided prophylactically, the agent(s) are provided in advance of any decrease in the number of B cells or serum antibody levels present in the host. The prophylactic administration of the agent(s) serves to prevent or attenuate any subsequent reduction in B cell number. When provided therapeutically, the agent(s) are provided at (or shortly after) the onset of a reduction in the number of B cells or antibodies present in a blood sample. The therapeutic administration of the compound(s) serves to attenuate any actual reduction in B cell number or antibody levels.

The agents of the present invention are administered to the mammal in a pharmaceutically acceptable form and in a therapeutically effective concentration. A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The agents of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in *Remington's Pharmaceutical Sciences* (16th ed., Osol, A., Ed., Mack, Easton, Pa. (1980)). In order to form a pharmaceutically acceptable composition suitable for effective administration, such compositions will contain an effective amount of one or more of the agents of the present invention, together with a suitable amount of carrier vehicle.

Additional pharmaceutical methods may be employed to control the duration of action. Control release preparations may be achieved through the use of polymers to complex or absorb one or more of the agents of the present invention. The controlled delivery may be exercised by selecting appropriate macromolecules (for example polyesters, polyamino acids, polyvinyl, pyrrolidone, ethylenevinylacetate, methylcellulose, carboxymethylcellulose, or protamine, sulfate) and the concentration of macromolecules as well as the methods of incorporation in order to control release. Another possible method to control the duration of action by controlled release preparations is to incorporate agents of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly(methylmethacrylate) microcapsules, respectively, or in colloidal drug delivery systems, for example, liposomes, albumin microspheres, microemulsions, nanoparticles, and nanocapsules or in macroemulsions. Such techniques are disclosed in *Remington's Pharmaceutical Sciences* (16th ed., Osol, A., Ed., Mack, Easton, Pa. (1980).

Having now generally described the invention, the same will be more readily understood through reference to the following examples which are provided by way of illustration, and are not intended to be limiting of the present invention, unless specified.

EXAMPLES

Example 1 Identification of Factors Involved in B Cell Proliferation and Differentiation A. Separation of Cell Contact and Lymphokine Signals Although the role of lymphokines seems to be inducing B cell differentiation and not in initiating activation events, both cell contact and lymphokines appear essential for generating an antibody response. Whether cell contact and lymphokine signals exerted distinct effects on resting B cells needed to be clearly evaluated. Additionally, the identity of the lymphokines that supported B cell activation, differentiation, and isotype switching were not clear. Because the Th2 cell clone D10 could provide all the necessary contact and lymphokine-dependent signals to resting B cells this antigen-specific clone was chosen for initial studies and preparation of plasma membranes. Antigen-independent activation of D10 cells was achieved by incubating cells with either the mitogen concanavalin A (Con A) or anti-CD3 antibodies adsorbed to plastic dishes. After harvesting, the cells were used to prepare membrane vesicles enriched for plasma membranes as described by Brian, A. A. (*Proc. Natl. Acad. Sci. USA* 85:564–568 (1988)), and the culture supernatant was used as a source of Th2 lymphokines by ultracentrifuging to remove any membrane components and absorbing any remaining Con A. Other studies have utilized similar methods for the preparation of plasma membrane-enriched fractions. (Noelle et al., *J. Immunol.* 146:1118–1124 (1991); Sekita et al., *Eur. J. Immunol.* 18:1405–1410 (1988)).

1. Role of Cell Contact

Membranes prepared from activated D10 Th cells induced strong proliferation of small resting B cells. The stimulatory activity was detectable by 3 hours of Th cell activation with Con A and peaked at 6 hours before declining to low levels. These kinetics followed closely those of lymphokine production by the same cells, suggesting a common regulatory pathway for both cell surface and secreted B cell stimulatory components. (Hodgkin et al., *J. Immunol.* 145:2025–2034 (1990)). Further evidence for a common signaling pathway was that the immunophilin binding immunosuppressant drug, cyclosporin A, (Bram et al., *Molec. Cell. Biol.* 13:4760–4769 (1993)) inhibited both lymphokine secretion and induction of B cell stimulatory activity (Hodgkin, P. D., and Kehry, M. R., *Advances in Molec. Cell. Immunol.* 1A: 127–160 Greenwich, Conn.: JAI Press, Inc. (1993)). Similar to early results of Stallcup et al. on the nonspecific inhibitory properties of plasma membranes, (Stallcup et al., *Cell. Immunol.* 89:144–150 (1984)) high doses of membranes from activated Th cells produced a nonspecific inhibitory effect on B cell proliferation (Hodgkin et al., *J. Immunol.* 145:2025–2034 (1990)).

A striking feature of B cell activation by Th membranes was that it was antigen independent and MHC unrestricted. In keeping with these observations Th membrane stimulation was polyclonal, inducing up to 70% of small resting B cells to enter S phase of the cell cycle within 48 hours of stimulation (Hodgkin et al., *J. Immunol.* 145:2025–2034 (1990)). Furthermore, the induced activity appeared to be an undescribed molecule as it was not blocked by antibodies to candidate molecules such as class II MHC, T cell receptor, CD4, LFA-1, Thy-1, or CD28. Thus, the contact signal in the absence of lymphokines appeared to deliver all the necessary signals for the induction of polyclonal B cell DNA synthesis.

B cells stimulated by activated Th cell membranes did not secrete immunoglobulin unless the lymphokine-containing supernatant from D10 cells was included in the culture. Notably, the amounts of the major immunoglobulin isotypes produced (IgM, IgG1, and IgE) resembled those generated by B cells stimulated directly by intact D10 cells. Thus, the antigen independent activation of B cells by Th membranes and lymphokines appeared to provide all the signals necessary to induce B cell proliferation, immunoglobulin class switching, and differentiation to immunoglobulin secretion (Hodgkin et al., *J. Immunol.* 145:2025–2034 (1990); Noelle et al., *J. Immunol.* 146:1118–1124 (1991)).

2. Role of Lymphokines

Th cell clones can be categorized by their lymphokine secretion profile following activation (Mosmann & Coffman, *Annu. Rev. Immunol.* 7:145–173 (1989)). Th1 T cells uniquely secrete IL-2 and IFN-γ and are generally poor stimulators of B cell immunoglobulin secretion in vitro. Th2 cells secrete IL-4 and IL-5 and induce strong immunoglobulin secretion from B cells. The different abilities to induce immunoglobulin secretion could be due either to differences in the lymphokines secreted or to an impairment of the Th1 cells to generate appropriate stimulatory cell surface ligands. To test these possibilities membranes were prepared from six different activated Th1 cell clones. Each stimulated strong B cell proliferation, and as with the Th2 membranes, the Th1 membranes alone induced no immunoglobulin secretion (Hodgkin et al., *J. Immunol.* 147:3696–3702 (1991)). When supernatants from activated Th2 cells were added to Th1 membranes the immunoglobulin isotopes secreted by B cells were identical to those secreted following activation with Th2 membranes and Th2 lymphokines. Furthermore, lymphokine-containing supernatants from each of the Th1 cell clones were unable to induce immunoglobulin secretion from B cells stimulated with membranes prepared form either Th1 or Th2 cells (Hodgkin et al., *J. Immunol.* 147:3696–3702 (1991)). Therefore it appears to be the lymphokine repertoire of Th1 cells and not an inability to provide contact-dependent signals that results in Th1 cells being poor B cell stimulators in vitro.

The Th2 lymphokines IL-4 and IL-5 both played a role in effecting differentiation of membrane-stimulated B cells to secrete immunoglobulin. The combination of recombinant IL-4 and IL-5 reproduced the ability of Th2 supernatants to induce IgM, IgG1, and IgE synthesis, and anti-IL-4 antibodies completely prevented immunoglobulin secretion (Hodgkin et al., *J. Immunol.* 145:2025–2034 (1990); Noelle et al., *J. Immunol.* 146:1118–1124 (1991)) (unpublished observations). The cytokines which are used for human B cell proliferation may be different from those used for mouse cell differentiation. A more detailed study of the combination of IL-4 and IL-5 revealed that the effect of each of these lymphokines was quite complex. IL-4 alone enhanced B cell proliferation induced by Th cell membranes (Hodgkin et al., *J. Immunol.* 145:2025–2034 (1990)). IL-4 was not essential for B cells to enter S phase of the cell cycle, but increased by about 10-fold the sensitivity of B cells to the Th membrane stimulus. In contrast, other lymphokines, including IL-5, had no effect on Th membrane-induced proliferation. IL-4 alone could also induce membrane-stimulated B cells to secrete immunoglobulin (Hodgkin et al., *J. Immunol.* 145:2025–2034 (1990)). However, there was a marked dose response disparity; enhancement of B cell proliferation required 100-fold less IL-4 than induction of immunoglobulin secretion. The effect of IL-5 appeared to be to enhance the ability of IL-4 to induce B cell differentiation to immunoglobulin secretion, exerting its greatest effect at low IL-4 concentrations. It is also clear that the inability of IL-4 alone to induce Th1 membrane-stimulated B cells to secrete immunoglobulin (Noelle et al., *J. Immunol.* 146:1118–1124 (1991); Hodgkin et al., *J. Immunol.* 147:3696–3702 (1991)) can be explained both by this dose-response disparity and by the presence of residual IFN-γ in Th1 membrane vesicles, since B cells stimulated by Th1 membranes and IL4 in the presence of anti-IFN-γ synthesize large quantities of immunoglobulin (unpublished observations).

The ability of the Th membrane system to separate discrete events in B cell activation allowed us to determine when lymphokines were required to induce immunoglobulin secretion. By initiating cultures with Th membranes and adding or removing D10 supernatant after various times we found that lymphokines were critically required during a window of time that corresponded closely to the period of B cell proliferation (Hodgkin et al., *Eur. J. Immunol.* 24:239–246 (1994)). These experiments indicated that the lymphokine-dependent commitment to differentiate into an immunoglobulin secreting cell occurred before the first round of cell division. Furthermore, the longer the cells were exposed to lymphokines during proliferation the more likely they were to differentiate to secrete IgE. Time course experiments demonstrated that IgM secreting cells first appeared in cultures at day 3 and preceded IgG1 secreting cells by 24 hours. IgE secreting cells appeared at day 5 and increased in number as the number of IgM secreting cells was declining.

B. Architecture of B Cell Activation by TH Cell Membranes

Many features of the mechanism by which molecules activate B cells were characterized by studies designed originally to biochemically isolate and reconstitute Th cell surface molecules in membrane vesicles. Detergent solubilization of Th membranes was originally shown to eliminate the ability of these membranes to activate resting B cells. However, a soluble fraction could be used to compete with the ability of intact Th membranes to stimulate B cell proliferation (M.R.K. unpublished observations). Because washing Th membranes with 3M salt solutions had no effect on the activity (M.R.K. unpublished observations) the B cell activating molecules appeared to be integral membrane proteins.

The physical character of active Th membrane vesicles was examined by assaying membrane activity at various times during preparation and after brief sonication. In parallel with the biological assays, transmission electron microscopy was performed on each membrane preparation (Kehry et al., "Mechanisms of Lymphocyte Activation and Immune Regulation IV": *Cellular Communications*, Plenum Press, New York (1992), pp. 139–148). It was found that membrane vesicles freshly prepared and centrifuged onto a sucrose pad contained low activity and were mostly individual and unaggregated. After ultra-centrifugation into a pellet and resuspension, these vesicles had maximal activity in stimulating B cell proliferation and consisted of many extremely large aggregates. Similarly, sonication of active membrane vesicles reduced their activity and produced small unaggregated vesicles. Ultra-centrifugation of sonicated vesicles restored full activity and produced larger aggregates (Kehry et al., "Mechanisms of Lymphocyte Activation and Immune Regulation IV": *Cellular Communications*, Plenum Press, New York (1992), pp. 139–148). These results suggested that Th membrane vesicles with maximal B cell stimulating activity were actually vesicle aggregates that would be capable of extensively crosslinking the B cell surface.

The binding and fate of Th membrane vesicles in cultures with resting B cells was also examined. B cells could be visualized by staining with anti-B220 antibody and, since anti-CD4 did not block the ability of the Th membranes to activate B cells, (Hodgkin et al., *J. Immunol.* 145:2025–2034 (1990)) anti-CD4 could be used to visualize Th membrane vesicles bound to B cells. The extensively aggregated Th membranes were bound to B cells by 24 hours of culture, and aggregation of the B cells was induced maximally by 72 hours. Although over the course of 4 days (by which time maximal B cell proliferation was occurring) the Th membrane vesicles deaggregated, contact between Th membranes and the B cells was maintained and no internalization or capping of membrane vesicles was observed (Kehry et al., "Mechanisms of Lymphocyte Activation and Immune Regulation IV": *Cellular Communications, Plenum Press, New York* (1992), pp. 139–148).

It was also found that washing B cells stimulated by Th membranes with ice cold buffer containing divalent metal ion chelating agents could arrest functional B cell stimulation. This was used to examine the length of time of Th membrane-B cell contact required for the induction of B cell proliferation. Th membranes were washed out after various times of culture, and it was found that although contact occurred early, an extended contact period (24–36 hours) between B cells and Th membranes was required to induce maximal B cell growth. This implied that resting B cells require continuous signaling over this period to achieve induction of DNA synthesis (Kehry et al., "Mechanisms of Lymphocyte Activation and Immune Regulation IV": *Cellular Communications*, Plenum Press, New York (1992), pp. 139–148). Thus, B cell activating molecules needed to extensively crosslink the B cell surface and provide functional signals over at least 24 hours in order to drive resting B cells to proliferate.

C. Identity of a Receptor-Ligand Pair

Initial characterization of the B cell activating molecules involved in delivering the contact signal to resting B cells came from biochemical studies on active Th cell membranes (Hodgkin et al., *J. Immunol.* 145:2025–2034 (1990)). By employing numerous washing, proteolysis, and detergent solubilization techniques, B cell activating molecules were found to be integral membrane proteins that required new mRNA and protein synthesis for their expression. In all respects B cell activating molecules were lymphokine-like components of the activated Th cell membrane: (Hodgkin et al., *J. Immunol.* 145:2025–2034 (1990)) they were synthesized de novo after Th cell activation; their synthesis by activated Th cells was rapid and transient; and they exerted their effects on other cell types in a noncognate manner. In the first step towards identifying the B cell activating molecules, Lederman et al. isolated an antibody to a Th cell-specific molecule that exhibited all of the above characteristics (Lederman et al., *J. Exp. Med.* 175:1091–1101 (1992)). A simultaneous approach considered possible candidates for a constitutively expressed receptor for B cell activating molecules on the resting B cell surface. Several lines of evidence suggested that a probable B cell receptor for B cell activating was the CD40 molecule. Stimulation of human B cells by antibodies to CD40 in the presence of lymphokines appeared to reproduce many of the features of Th-dependent B cell activation, proliferation, and differentiation (Jabara et al., *J. Exp. Med.* 172:1861–1864 (1990); Rousset et al., *J. Exp. Med.* 173:705–710 (1991); Zhanget al., *J. Immunol.* 146:1836–1842 (1991); Banchereau et al., *Science* 251:70–72 (1991)). CD40 belongs to the TNF receptor family whose members are characterized by repeated Cys-rich extracellular domains. By functional homology with TNF receptor a search for a soluble ligand for CD40 had been underway (Clark, E. A., *Tiss. Antigens* 35:33–36 (1990)). However, the activity of anti-CD40 antibodies and the ability of these antibodies immobilized on Fc receptor expressing L cells to induce long term human B cell growth (Banchereau et al., *Science* 251:70–72 (1991)) made it possible that a ligand for CD40 could be membrane-bound.

Several laboratories produced a soluble form of CD40 that linked the extracellular domain of human CD40 to the Fc portion of human IgG1 (Fanslow et al., *J. Immunol.* 149:655–660 (1992); Castle et al., *J. Immunol.* 151:1777–1788 (1993)). This fusion protein was capable of blocking Th cell-dependent B cell activation (Castle et al.,*J. Immunol.* 151:1777–1788 (1993); Noelle et al., *Proc. Natl. Acad. Sci. USA* 89:6550–6554 (1992)) and was used to identify and clone a ligand for CD40 (Armitage et al., *Nature* 357:80–82 (1992)). The CD40 ligand was identified as a 33,000–35,000 MW glycoprotein that was not covalently associated with other proteins and was expressed by activated T cells. When recombinant CD40 ligand was expressed on the surface of fibroblasts, it was capable of stimulating B cell proliferation, albeit at relatively low levels (Armitage et al., *Nature* 357:80–82 (1992)). Concurrently, antibodies were produced that recognized both human (Lederman et al., *J. Exp. Med.* 175:1091–1101 (1992)) and mouse (Noelle et al., *Proc. Nati. Acad. Sci. USA* 89:6550–6554 (1992)) B cell activating molecules. These antibodies had the property of blocking Th cell-dependent cell activation events and were demonstrated to recognize the ligand for CD40.

CD40 ligand has all the properties of B cell activating molecules and of a membrane-associated lymphokine (Farrah & Smith, *Nature* 358:26 (1992)). The most striking structural features of CD40 ligand are its homology with TNF-$\alpha$ and TNF-$\beta$ (Farrah & Smith, *Nature* 358:26 (1992); Smith, Cell 76:959–962 (1994)) and its probable orientation as a type 2 membrane glycoprotein. Regulation of expression of the CD40 ligand gene in Th cell clones was found to be similar to that of IL-2 gene regulation, (Castle et al., *J. Immunol.* 151:1777–1788 (1993)) again suggesting that CD40 ligand is a member of a new class of membrane-associated lymphokines. This is supported by the recent cloning of related cell surface ligands for two other members of the TNF receptor family, CD27 (Goodwin et al., *Cell* 73:447–456 (1993)) and CD30 (Smith et al., *Cell* 73:1349–1360 (1993)). The critical role of CD40 ligand in Th cell-dependent B cell activation has been demonstrated by correlating an immunodeficiency disease, X-linked hyper-IgM syndrome, to a lack of expression of functional CD40 ligand on Th cells. The defect results from a variety of mutations in the CD40 ligand gene (Allen et al., *Science* 259:990–993 (1993); Aruffo et al., *Cell* 72:291–300 (1993); Korthauer et al., *Nature* 361:539–541 (1993); DiSanto et al., *Nature* 361:541–543 (1993)). This syndrome is characterized by the absence of switched IgG-, IgA-, and IgE-secreting B cells and a lack of the corresponding antibody.

Recent studies of several forms of recombinant human and mouse CD40 ligand have increased our understanding of the requirements of resting B cells for induction of activation and proliferation events. As a fusion protein with the extracellular domain of CD8$\alpha$, soluble CD40 ligand has been found to have a low level of activity for stimulating B cell proliferation (Lane et al., *J. Exp. Med.* 177:1209–1213 (1993); Hollenbaugh et al.,*EMBO J.* 11:4313–4321 (1992)). In the absence of external crosslinking soluble CD40 ligand primarily acted as a costimulator of B cell proliferation in conjunction with phorbol esters, anti-CD20, or anti-$\mu$ (Lane et al., *J. Exp. Med.* 177:1209–1213 (1993); Hollenbaugh et al., *EMBO J.* 11:4313–4321 (1992)). We have observed that the CD8–CD40 ligand fusion protein is capable of driving resting B cell proliferation only after crosslinking with anti-CD8 or when used as a costimulator with Th2 lymphokines (B. Castle and M.R.K., *Sem. Immunol.* 6:287–294 (1994)) or surface IgM or IgD cross linking (Snapper, C. M. et al., *J. Immunol.* 154:1177–1187 (1995)). Because soluble CD40 is not monomeric (B. Castle and M.R.K., unpublished observations), this implies that resting B cells require a high degree of CD40 crosslinking for the induction of proliferation. Additionally, IL-4 appears to increase the sensitivity of resting B cells to low levels of CD40 crosslinking, as has been found using anti-CD40 antibodies (Clark, E. A., *Tiss. Antigens* 35:33–36 (1990); Rousset et al., *J. Exp. Med.* 173:705–710 (1991); Gordon et al., *Eur. J. Immunol.* 17:1535–1538 (1987)). Similar responses have been found using IL-4 and anti-$\mu$ antibodies (Hodgkin et al., *Cell. Immunol.* 134:14–30 (1991)). Thus, under conditions that induce extensive crosslinking, CD40 ligand appears to be sufficient to activate resting B cells. Under suboptimal crosslinking conditions, CD40 ligand acts as a costimulator with lymphokines or other B cell surface molecules. Which conditions of B activation are similar to those induced by normal Th cells remains to be determined.

The ability of Th2 lymphokines to costimulate B cell proliferation with soluble CD40 ligand provides an explanation of a discrepancy in the effects of IL-4 on B cell proliferation induced by Th membranes (Hodgkin et al., *J. Immunol.* 145:2025–2034 (1990); Noelle et al., *J. Immunol.* 146:1118–1124 (1991)). In one study, it was found that Th membranes were capable of stimulating increases in resting B cell RNA synthesis, but required the addition of IL-4 to effect DNA synthesis (Noelle et al., *J. Immunol.* 146:1118–1124 (1991)). In a different study, it was found that Th membranes were capable of stimulating B cell proliferation in the absence of added lymphokines, although IL-4 significantly enhanced B cell proliferation (Hodgkin et al., *J. Immunol.* 145:2025–2034 (1990)). It is now known that the recombinant membrane form of CD40 ligand alone is capable of stimulating B cell proliferation (Armitage et al., *Nature* 357:80–82 (1992)) (see below). It appears that the methods used for preparing Th membranes in the two studies may have differed so that in one case, where a different homogenization protocol was performed on activated Th cells, (Noelle et al., *J. Immunol.* 146:1118–1124 (1991)) smaller less aggregated vesicles may have resulted. These would be analogous to sonicated Th membrane vesicles described above (Kehry et al., "Mechanisms of Lymphocyte Activation and Immune Regulation IV": *Cellular Communications*, Plenum Press, New York (1992), pp. 139–148) or soluble CD40 ligand and would require costimulation to induce B cell proliferation.

CD40 ligand has also been expressed transiently as the membrane form in fibroblasts. Although this material is also sufficient to induce B cell proliferation, the extent of the response is greatly decreased from that obtained by intact Th cells (Armitage et al., *Nature* 357:80–82 (1992); Grabstein et al., *J. Immunol.* 150:3141–3147 (1993)). In the presence of the appropriate lymphokines and recombinant membrane CD40 ligand, B cell differentiation occurs (Grabstein et al., *J. Immunol.* 150:3141–3147 (1993); Armitage et al., *J. Immunol.* 150:3671–3680 (1993); Spriggs et al., *J. Exp. Med.* 176:1543–1550 (1992); Maliszewski et al., *Eur. J. Immunol.* 23:1044–1049 (1993). However, there appear to be some differences in the lymphokine requirements between B cells stimulated with Th cells and recombinant CD40 ligand (Grabstein et al., *J. Immunol.* 150:3141–3147 (1993); Armitage et al., *J. Immunol.* 150:3671–3680 (1993) ). Recent studies also have shown a discrepancy between the level of CD40 ligand expression and the ability of Th cells to drive B cell proliferation (Castle et al., *J. Immunol.* 151:1777–1788 (1993); Roy et al., *J. Immunol.* 151:2497–2510 (1993)). It appears that newly synthesized CD40 ligand in Th cells is not fully competent to deliver the contact signal to resting B cells. There may be some requirement for associations with other Th cell surface proteins (i.e. costimulator B cell activating molecules) or for assembly of newly synthesized CD40 ligand with itself or with the cytoskeleton (Castle et al., *J. Immunol.* 151:1777–1788 (1993)). It is possible that a certain density of CD40 ligand could be critical in inducing maximal B cell responses. It appears, from these studies, that additional B cell activating molecules may remain to be discovered.

The characteristics of CD40 ligand as a B cell activating molecule are also consistent with the inability to reconstitute B cell proliferative activity after detergent solubilization of Th cell membranes (described above). The homologies CD40 ligand shares with TNF-$\alpha$ and TNF-$\beta$ are restricted to particular $\beta$-sheet regions of the TNF molecules that are involved in forming an associated trimer structure (Farrah & Smith, *Nature* 358:26 (1992)). This implies that a native quaternary structure of membrane CD40 ligand may be a trimer. Because CD40 ligand is not disulfide-linked to itself, such a structure may be expected to dissociate upon detergent solubilization and reform only under very specific conditions. Additionally if noncovalent associations with other Th cell membrane proteins or costimulators are required to induce crosslinking of the B cell surface for a maximal proliferative response, these may also readily dissociate upon detergent solubilization.

D. Placing B Cell-Th Cell Interaction in an In Vivo Context

In the spleen B cell activation and proliferation occur in two sites, the proliferative foci and the germinal center. To initiate the foci, which are first detectable 2 to 3 days after immunization, the antigen stimulated B cell migrates to the T cell rich outer periarteriolar lymphoid sheath (PALS) areas of the splenic white pulp (Kupfer & Singer, *J. Exp. Med.* 170:1697–1713 (1991)). If contact is made with an appropriate T cell, proliferation of both T and B cells takes place and the B cells switch and secrete IgG subclasses. They may also migrate along terminal arterioles to the red pulp, possibly exiting the spleen (Van Rooijen, N., *Immunol. Today* 11:436–439 (1990)). Most of the primary antibody in an immune response arises from B cells in these foci (Tsiagbe et al., *Immunol. Rev.* 126:113–141 (1992)). The germinal center response is initiated a few days after the formation of foci. Germinal center B cells are possibly derived from B cells activated in the foci (Jacob & Kelsoe, *J. Exp. Med.* 176:679–687 (1992)). The germinal center is a site of intense B cell proliferation necessary for the generation and selection of B cells producing higher affinity hypermutated antibodies.

The mechanism of B cell activation, reproduced in vitro by Th membranes and lymphokines, closely resembles the mechanism of B cell activation in the primary proliferative foci seen in vivo (Kehry, M. R., and Hodgkin, P. D., *Sem. Immunol.* 5:393–400 (1993)). Recent elegant immunohistochemical studies of the in situ localization of CD40 ligand in lymphoid organs of immunized mice are consistent with this conclusion. CD40 ligand was only found on T cells in the outer PALS region or associated with terminal arterioles (Van der Eertwegh et al., *J. Exp. Med.* 178:1555–1656 (1993)). Additionally the kinetics of CD40 ligand appearance correlated with those of foci formation rather than of the kinetics of germinal center formation. In fact no CD40 ligand was observed in germinal centers.

E. A New System for Studying B Cell-T Cell Interaction

Because it has not been possible to keep normal untransformed B cells alive in vitro for extended periods of time. (Tisch et al., *Immunol. Today* 9:145–150 (1988)) the existing in vitro systems for studying B cell responses utilize freshly isolated B cells from spleen, tonsils, or peripheral blood. These B cell populations are inherently different and heterogeneous, and this variability may be responsible for many differing experimental results not only between different laboratories, but between mouse and human B cell studies. It has not been possible to establish B cell lines that are analogous to T cell clones (Tisch et al., *Immunol. Today* 9:145–150 (1988)). On the average, cultured B cells remain alive for less than 2 days in the absence of stimulation. Once activated in vitro by Th cells, B cells appear to undergo 2 to 3 rounds of cell division, and when Th2 lymphokines are present, they will differentiate to secrete antibody (Hodgkin et al., *Eur. J. Immunol.* 24:239–246 (1994)). However, after the initial proliferation period, extensive B cell death occurs, so that actual viability after 7 days may be less than 10% (Hodgkin et al., *Eur. J. Immunol.* 24:239–246 (1994)). This has made it impossible to establish in vitro systems for studying some of the poorly understood aspects of a B cell response: for example, signals that generate memory B cells and the molecular mechanisms that drive somatic mutation and selection of high affinity antibody producing cells. A system that utilized IL-4 and anti-CD40 antibodies immobilized on Fc receptor positive fibroblasts to grow human B cells for extended periods of time (Rousset et al., *J. Exp. Med.* 173:705–710 (1991); Banchereau et al., *Science* 251:70–72 (1991); Galibert et al., *J. Immunol.* 152:22–29 (1994)) has been the closest approximation to a B cell line. However, the cell doubling time was slow, (Galibert et al., *J. Immunol.* 152:22–29 (1994)), and the requirement for IL-4 generated antibody producing cells in the heterogeneous culture (Banchereau et al., *Science* 251:70–72 (1991)).

Example 2 Efficient Proliferation and Differentiation of B Cells Using hdmb Cd40 Ligand Materials and Methods The construction and isolation of a recombinant baculoviral vector which directs the expression of high density membrane bound mouse CD40 ligand was as follows. The transfer vector used in this study is a derivative of the plasmid $ph_{v1}360$, a gift of Dr. Charles Has and Dr. J. Donald Capra (Southwestern Medical Center, Dallas, Tex.) (Hasemann and Capra, *Proc. Natl. Acad. Sci. USA* 87:3942–3946 (1990). Plasmids containing the cDNA encoding murine CD40 ligand and the murine CD40 ligand are known in the art. To insert the CD40 ligand cDNA into the transfer vector, PCR mutagenesis was utilized to introduce an Nco I site exactly coincidentally with the ATG initiation codon of the CD40 ligand cDNA and an Xba I site immediately distal to the translation termination codon. The amplified DNA was initially cloned into PTZ19R and then subcloned into $ph_{v1}360$ after the immunoglobulin heavy chain cDNA was removed by Nco I/Xba I digestion. The resulting plasmid was cotransfected with AcMNPV viral DNA via the $CaCl_2$ precipitation procedure. Occlusion negative viral plaques were isolated and plaque purified using standard techniques (Summers and Smith, Texas Agricultural Experiment Station Bulletin (1987), p. 1555).

A high titer virus stock grown in SF9 cells using standard techniques (O'Reilly et al., *Baculovirus expression vectors, a laboratory manual*, W. H. Freeman and Company, New York, N.Y. (1992)) was used to infect Sf9 cells grown in suspension culture for 66 h at 27° C. (MOI of 100). Infected SF9 cells were harvested by centrifugation, washed twice with ice cold Rinaldini's salt solution (Sigma Chemical Co., St. Louis, Mo.) containing 1.0 mM $CaCl_2$, and membranes were prepared as described (Hodgkin et al., *J. Immunol.* 145:2025 (1990): Brian, *Proc. Natl. Acad. Sci. USA* 85:564 (1988); Maeda et al., *Biochim. Biophy. Acta* 731:115 (1983)). Membranes, designated hdmb mouse CD40 ligand, were washed and resuspended in Dulbecco's PBS and stored under liquid nitrogen. Total membrane protein concentration was determined for each preparation (Micro BCA assay, Pierce). Batches of membranes were titrated in a B cell proliferation assay (see below).

Human B Cell preparation. Highly purified B cells were prepared as described (Amoroso and Lipsky, *J. Immunol.* 145:3155 (1990)). Briefly, PBMC were prepared from heparinized blood of healthy adults by centrifugation over sodium diatrizoate/ficoll gradients (Pharmacia, Inc., Piscataway, N.J.). PBMC were resuspended in serum free RPMI 1640 and treated with 5 mM L-leucine methyl ester HCl for 45 min at room temperature in order to deplete monocytes and natural killer cells. Non-resetting cells consisting largely of B cells were collected and treated with 100 $\mu$M L-leucyl-leucine methyl ester for 15 min at room temperature to deplete any remaining NK cells and monocytes (Thiele and Lipsky, *J. Immunol.* 136:1038 (1986)). Following this treatment, cells were rosetted again and the SRBC rosette forming cells were removed by centrifugation. B cells prepared in this manner were more than 90% pure as indicated by staining with mAb to CD20 or CD19. Alternatively, B cells can be purified using anti-CD19 coated magnetic beads as described by the manufacturer (Dynabeads from Dynal).

Mouse B cell preparation. Mouse B cells were prepared as described by Hodgkin et al., *J. Immunol.* 145:2025–2034 (1990).

Cytokines. Supernatant from activated D10.G4.1 (D10) cells was obtained as previously described (Hodgkin et al., *J. Immunol.* 145:2025 (1990)). Briefly, D10 Th2 cells grown in petri dishes for 3 weeks post-stimulation were harvested, washed twice in medium lacking IL-2, and stimulated with 5 $\mu$g/ml concanavalin A (Sigma Chemical Co., St. Louis, Mo.) for 9 h. After removal of cells by low speed centrifugation, supernatant was centrifuged at 95,000×g, filtered through a 0.22 $\mu$m membrane and absorbed on a mannose-agarose column (E-Y Laboratories, San Mateo, Calif.). D10 supernatant was titrated in B cell proliferation and antibody production assays and used at a final dilution of 1/100. Additionally, cytokines produced by other cell types, including but not limited to dendritic cells, follicular dendritic cells, and other antigen presenting cells, in the presence or absence of specific antigen, can be included in the cultures.

Culture conditions. B cells were grown in B cell medium (BCM): 10% fetal calf serum (Hyclone characterized); 10 mM Hepes pH 7.3; L-glutamine; Penicillin/Streptomycin; non-essential amino acids; sodium pyruvate; and $5\times10^{-5}$M 2-mercaptoethanol, in RPMI-1640. The medium and 100× supplements were obtained from Gibco.

For long term growth experiments, B cells were cultured in V-bottom 96 well microtiter plates (001-010-2701, Dynatech Laboratories, Inc., Chantilly, Va.) in 150 $\mu$l BCM at 37° C., 5.5% $CO_2$. Initially, hdmb mouse CD40 ligand was (3 $\mu$g/ml final concentration) with or without D10 sn (1/100 final dilution) were added in 100 $\mu$l BCM. Small dense B cells (1,000/well) were added in 50 $\mu$l BCM. Every 48 hours plates were fed fresh medium components as follows. Plates were centrifuged at 1600 rpm for 7 minutes (GS-6KR centrifuge, Beckman), medium was aspirated leaving~15 $\mu$l, and fresh medium (150 $\mu$l) was added.

Antibody measurement. Supernatants from the cultures were harvested for antibody assays by removing 140 $\mu$L culture supernatant from three replicate sample wells. 140 $\mu$L BCM were added back to the wells and 140 $\mu$L removed for residual antibody concentration. These wells were not used further. IgM, IgG, and IgE levels were measured by isotype-specific ELISA as described previously (Hodgkin et al., *J. Immunol.* 145:2025–2034 (1990); Hodgkin et al., *Eur. J. Immunol.* 24:239–246 (1994)). Residual levels of each isotype in each well after replacement with fresh medium (carry over to next time point) were subtracted from each value.

Results

Figure 2B:
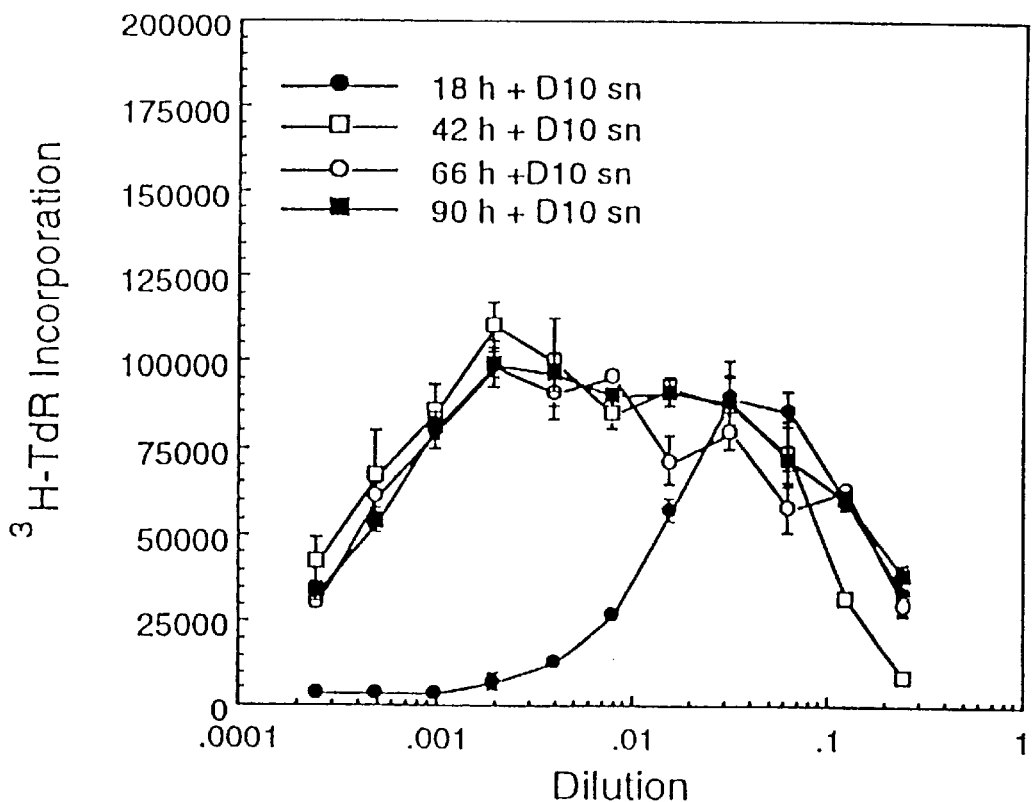

SF9 cells were infected with a recombinant baculovirus containing mouse CD40 ligand for various times (FIG. 2). An enriched plasma membrane fraction was prepared and each membrane preparation titrated in a B cell proliferation assay ($2\times10^4$ B cells/well for 72 h). Using incorporation of a radiolabeled compound as a marker for cell division, maximum incorporation of $^3$H-TdR (4 h pulse) was observed with membranes prepared from 66 h infected SF9 cells (66 h hdmb CD40 ligand). When the hdmb CD40 ligand was used to stimulate B cells in the presence of D10 sn (1/100; lymphokine-containing supernatant from 9 h stimulated D10.G4.1 Th2 T cell clone, Hodgkin et al., 1990), plasma membranes from 42 h, 66 h, and 90 h infected SF9 cells were equivalent in their ability to stimulate B cells (FIG. 2B).

To demonstrate that the proliferation response observed was mediated by hdmb CD40 ligand, B cells ($2\times10^4$/well) were stimulated with a constant amount of hdmb CD40 ligand (1/200) in the presence and absence of an CD40-IgG1 fusion protein (Castle et al., *J. Immunol.* 151:1777–1788 (1993) (FIG. 3). Filled circles, CD40-IgG included (35 μg/ml at the highest concentration); open squares, no CD40-IgG. The proliferation produced by the hdmb CD40 ligand could be specifically inhibited by CD40-IgG, demonstrating that proliferation was induced by hdmb CD40 ligand.

To determine the effects of density on cell proliferation, B cells were placed into 96 well plates ($1\times10^4$/well) with hdmb CD40 ligand (1/80) and D10 sn (1/100). The cells were counted and the media replaced every 48 h. At days 5 and 8 the cells were resuspended and split ⅛ (FIG. 4). Filled triangles, cells not split; filled circles, ⅛ split at day 5; filled squares, ⅛ split at day 8; open circles, ⅛ split multiplied by 8; open squares, second ⅛ split multiplied by 64. At input cell concentrations above $5\times10^4$/ml, reducing the cell number was necessary to obtain maximal proliferation.

To test various culture formats, B cells were placed in either flat bottom or "V" bottom 96 well plates ($1\times10^3$ cells/well). The cells were incubated with either hdmb CD40 ligand and D10 sn (++) or hdmb CD40 ligand only (+−). The cells were counted and medium was removed and replaced every 48 h (FIG. 5). Filled squares, hdmb CD40 ligand and D10 sn in flat bottom plate; open circles, hdmb CD40 ligand and D10 sn in "V" bottom plate; open squares, hdmb CD40 ligand in flat bottom plate; filled circles, hdmb CD40 ligand in "V" bottom plate. As shown in FIG. 5 when lymphokines were not present, higher numbers of B cells were recovered from plates with "V" bottom wells.

Figure 6A:
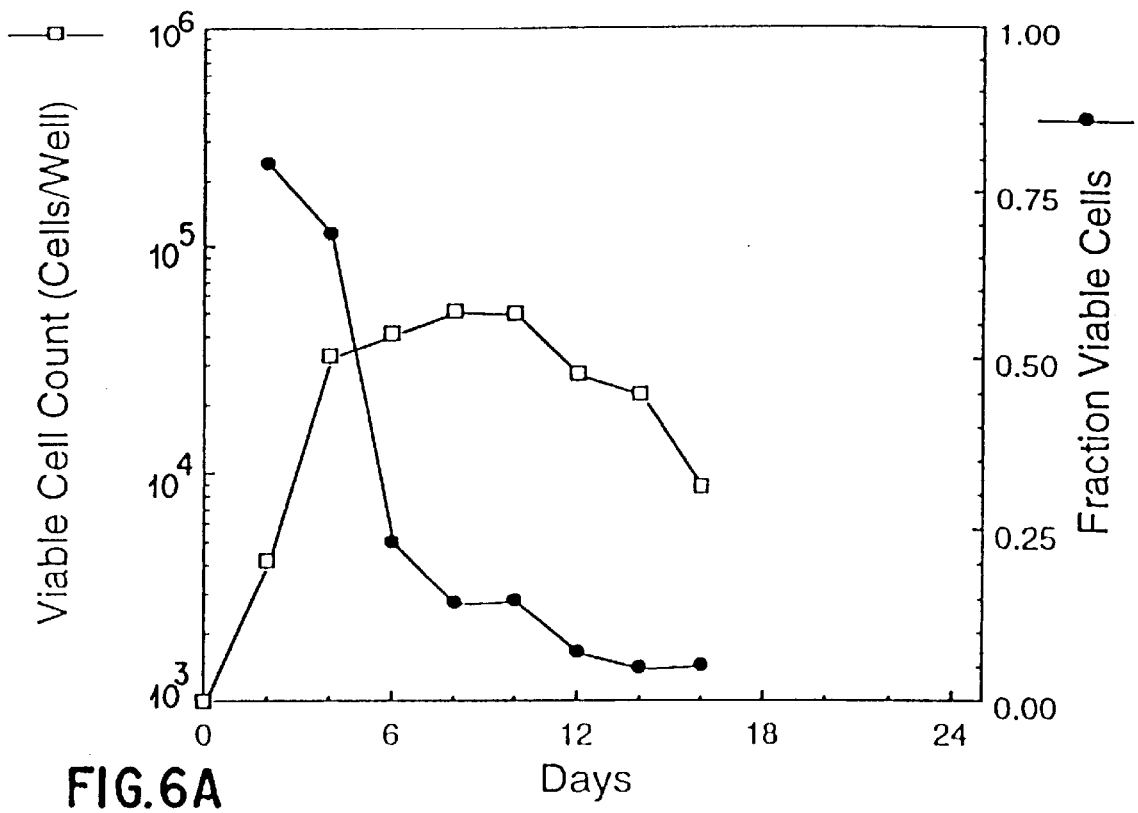

To assay for antibody secretion from proliferated and differentiated B cell, B cells were placed into a 96 well "V" bottom plates ($1\times10^3$ cells/well) with hdmb CD40 ligand (1/300) and D10 sn (1/100). Every 48 h cells were removed, counted, and the media was not replaced (FIG. 6A). Open squares, total number of viable cells; filled circles, fraction of cells which were viable.

Figure 6B:
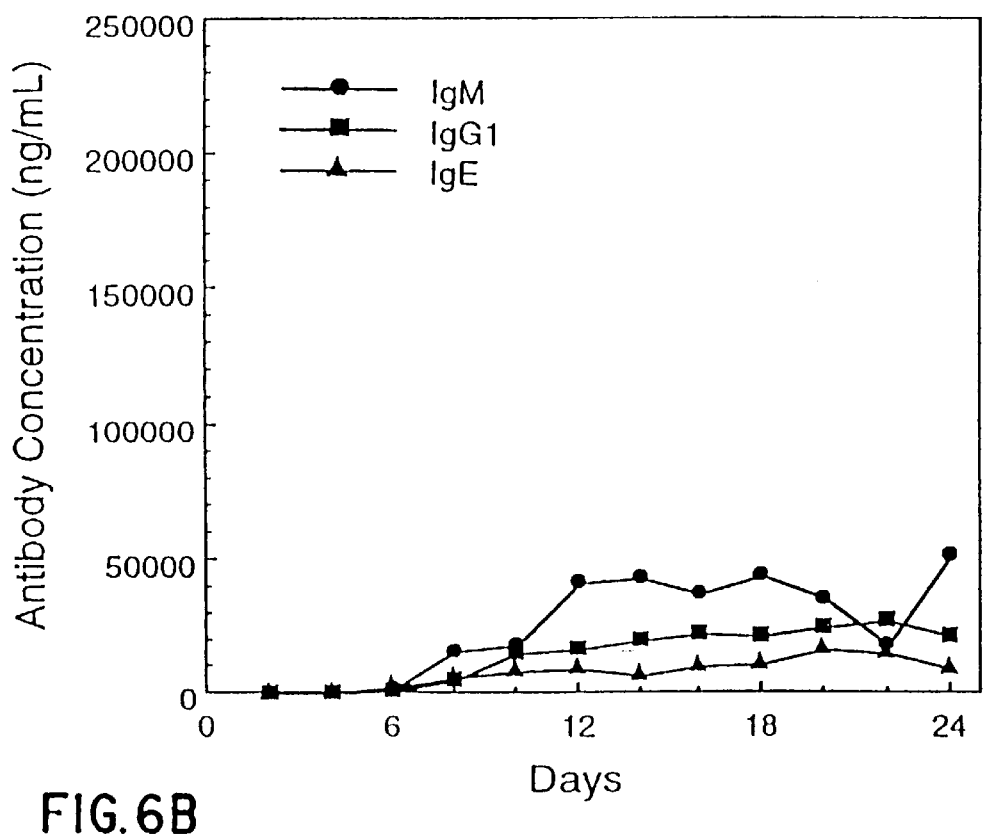

The medium from replicate wells was removed and antibody concentration was measured by quantitative ELISA (FIG. 6B). Filled circles, IgM; filled squares, IgG1; filled triangles, IgE. Cumulative antibody concentrations are provided in ng/ml. The maximum cell number occurred at approximately day 8 (50-fold increase in cell number) while the majority of IgM production occurred between days 8 and 12 (FIG. 6B).

Figure 7A:
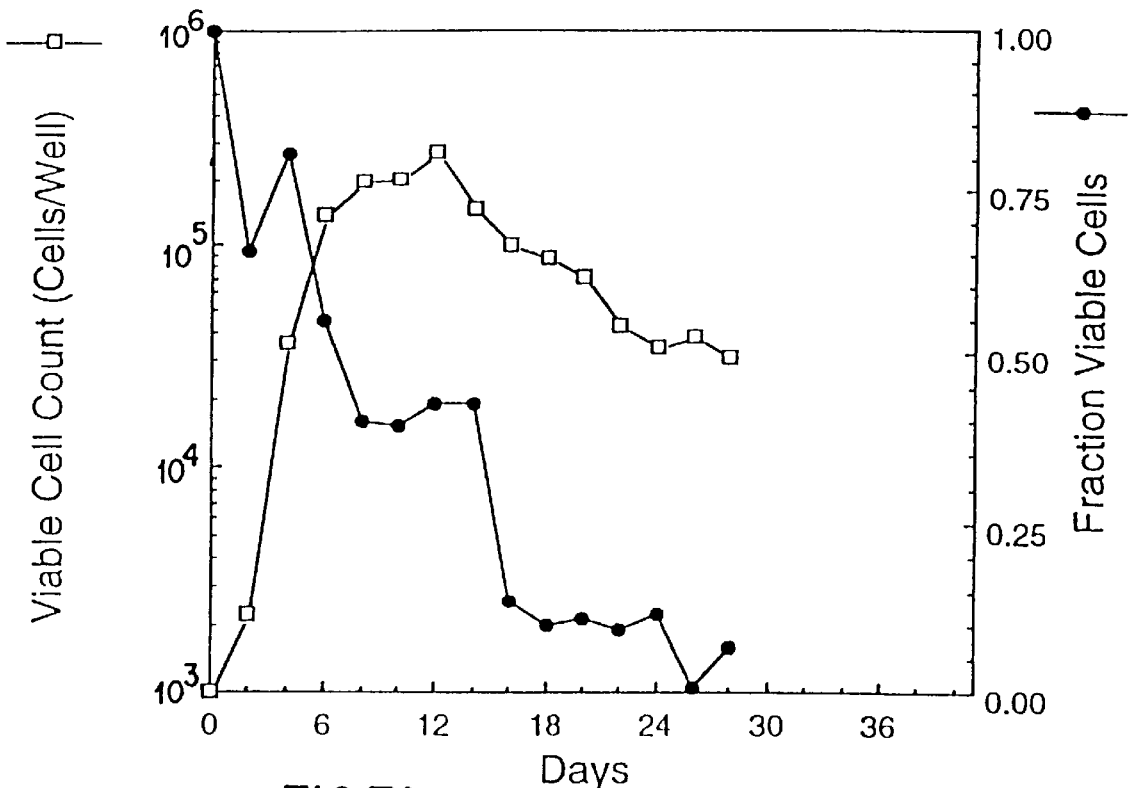

To determine the effect of medium replacement on B cell proliferation and differentiation, B cells were placed into a 96 well "V" bottom plates ($1\times10^3$ cells/well) with hdmb CD40 ligand (1/300) and D10 sn (1/100). Every 48 h, cells were removed and counted and the old medium was removed and replaced with fresh medium (FIG. 7A). Open squares, total number of viable cells; filled circles, fraction of cells which were viable.

Figure 7B:
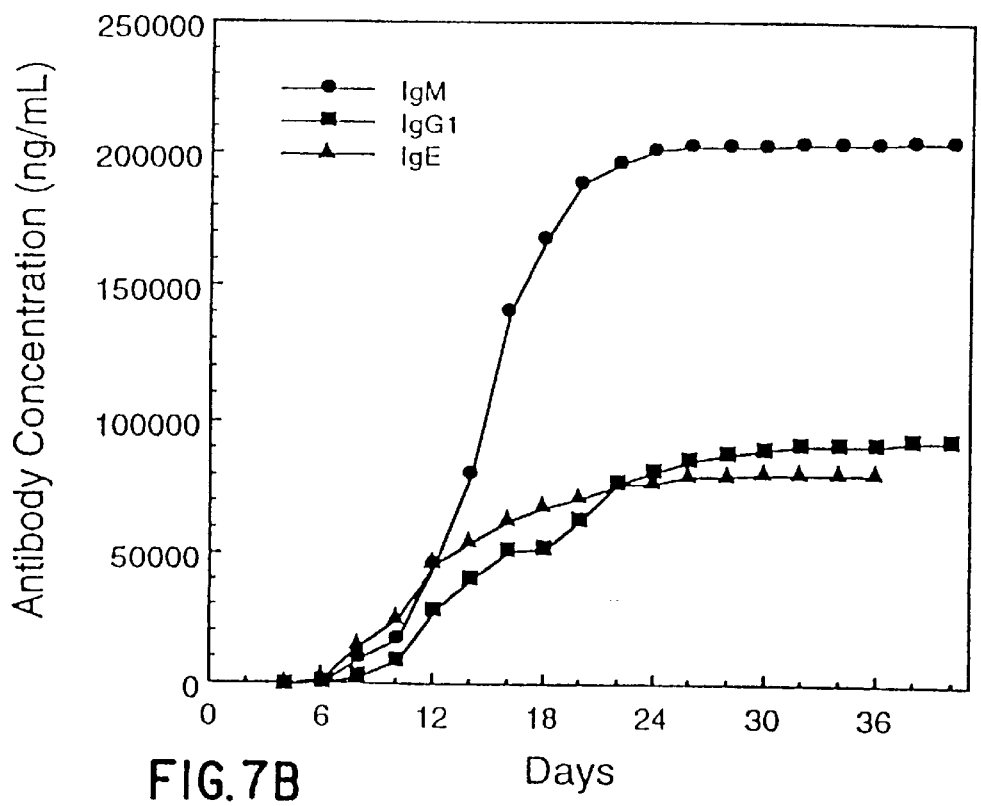

The medium from replicate wells was removed and antibody concentration was measured by quantitative ELISA (FIG. 7B). Filled circles, IgM; filled squares, IgG1; filled triangles, IgE. Cumulative antibody concentrations are provided in ng/ml. The maximum cell number occurred at approximately day 10 (200-fold increase in cell number) while the majority of IgM production occurred between days 8 and 22.

To test the effects of a multistep proliferation protocol on antibody secretion, B cells were placed into a 96 well "V" bottom plates ($1\times10^3$ cells/well) with hdmb CD40 ligand (1/300) and D10 sn (1/100) (FIG. 8). Every 48 h cells were removed and counted and the old medium was removed and replaced with fresh medium (FIG. 8); +−, medium contained hdmb CD40 ligand; −−, medium contained no additions; ++, medium contained hdmb CD40 ligand and D10 sn. Open squares, total number of viable cells; filled circles, fraction of cells which were viable.

The medium for replicate wells was removed and antibody concentration was measured by quantitative ELISA. Filled circles, IgM; filled squares, IgG1; filled triangles, IgE. Cumulative antibody concentrations are provided in ng/ml (FIG. 8). The maximum cell number occurred at approximately day 18 (100-fold increase in cell number) while the majority of IgM production occurred between days 16 and 34.

To determine the frequency at which B cells respond to hdmb CD40 ligand, B cells were plated at 1, 3, 10, and 30 cells/well in 96 well "V" bottom plates with either hdmb CD40 ligand (1/300) or hdmb CD40 ligand (1/300) and D10 sn (1/100) (FIG. 9). After 6 days, the cells were resuspended, transferred to flat bottom plates, and scored for the presence of divided viable cells. In cultures stimulated with hdmb CD40 ligand, approximately ⅛ of the B cells grew; in cultures stimulated with hdmb CD40 ligand and D10 sn, approximately ½ of the B cells grew.

To test the proliferative effect of hdmb CD40 ligand on human B-cells, human B cells were isolated and grown as described for the mouse cells and above (FIG. 10). Human B cells expanded at least 100-fold and Ig production was observed at day 10–14.

Example 3 Proliferation and Differentiation of Human B Cells

In the previous study, a method for proliferating and differentiating normal mouse B lymphocytes was established. The method involved the use of hdmb recombinant mouse CD40 ligand expressed in insect cells in combination with a source of cytokines capable of supporting B cell differentiation. Under these conditions, mouse B lymphocytes expanded ~250-fold and could be grown at high frequency as individual clones (1 in 2 cells responding). All B cell clones that expanded also differentiated to secrete high levels of IgM and/or IgG antibody. The purpose of the present study is to demonstrate that similar cellular expansion and differentiation using normal human B lymphocytes can be obtained using the herein disclosed methods. Using the present methods, human B cells gave an efficient proliferative response to hdmb recombinant human CD40 ligand expressed in insect cells in combination with human cytokines. It was possible to grow human B cell clones with high frequency and obtain differentiation to immunoglobulin secretion.

Materials and Methods

Antibodies and Reagents. Monoclonal anti-human CD3 (64.1) was produced by Dr. John Hansen (Fred Hutchison Cancer Center, Seattle, Wash.). Monoclonal anti-human CD3 used for panning, anti-human CD8, anti-human CD14, and anti-human CD19 were purchased from PharMingen (San Diego, Calif.). For quantitating human antibody levels by ELISA, $F(ab')_2$ goat anti-human IgM (purified and biotin-conjugated) and $F(ab')_2$ goat anti-human IgG (Fc-specific) (purified and biotin-conjugated), and streptavidin-HRP were from Jackson ImmunoResearch (West Grove, Pa.). For ELISPOT assays on mouse B cells, biotin conjugated goat anti-mouse IgM was from Zymed (So. San Francisco, Calif.) and biotin goat anti-mouse IgG was from Southern Biotechnology, Inc. (Birmingham, Ala.). Purified human myeloma IgM, IgG1, IgG2, IgG3, and IgG4 used as ELISA standards were obtained from The Binding Site, Ltd. (Birmingham, England). Purified keyhole limpet hemocyanin (Inject KLH) was from Pierce Chemical Co. (Rockford, Ill.).

Cytokines. Recombinant human IL-1a, IL-2, IL-4, IL-6, IL-10, and IL-11 were purchased from Genzyme (Cambridge, Mass.). Stock solutions were prepared by diluting each in B cell medium (BCM; see below), 0.2 $\mu$M filtering, and storing in aliquots at $-80°$ C.

Supernatants from activated human peripheral blood T cells were obtained as follows. Peripheral blood mononuclear cells obtained after centrifugation over Ficoll-Hypaque were panned sequentially on plates coated overnight with anti-CD14 (5 $\mu$g/ml), anti-CD14 and anti-CD19 (2.5 $\mu$g/ml each), and anti-CD8 (5 $\mu$g/ml). Panning was in Hank's balanced salt solution, 5% FBS, 10 mM HEPES, pH 7.3 at 4° C. for 1 h. Nonadherent cells were washed and resuspended at $4 \times 10^6$ cells/ml in warm BCM [RPMI 1640 supplemented with 10% FBS, 10 mM HEPES (pH 7.3), 2 mM L-glutamine (GIBCO, Grand Island, N.Y.), 0.1 mM nonessential amino acids (GIBCO), 1 mM sodium pyruvate, $5 \times 10^{-5}$M 2-mercaptoethanol, and 100 U/ml each penicillin and streptomycin (GIBCO)]. For anti-CD3 stimulation, cells were placed on tissue culture dishes coated with 4 $\mu$g/ml anti-CD3 for 48 h at 37° C. For stimulation with PHA/PMA, cells were incubated with 2.5 $\mu$g/ml PHA and 10 ng/ml PMA for 2 h at 37° C., washed and incubated in fresh warm BCM for 46 h at 37° C. After removal of cells by low speed centrifugation, supernatants were centrifuged at 100,000×g, filtered through a 0.2 $\mu$M membrane, and stored in aliquots at $-80°$ C.

Additionally, cytokines produced by other cell types, including dendritic cells, follicular dendritic cells, and other antigen presenting cells, in the presence or absence of specific antigen, can be included in the cultures as stimuli.

Baculovirus growth, insect cell infection, and preparation of membranes. A recombinant baculovirus encoding full length human CD40 ligand was constructed by standard techniques (O'Reilly, D. R., L. K. Miller, and V. A. Luckow. 1992. *Baculovirus expression vectors, a laboratory manual*. W. H. Freeman and Company, New York, N.Y.). A high titer virus stock grown in SF9 cells using standard techniques (O'Reilly, D. R., L. K. Miller, and V. A. Luckow. 1992. *Baculovirus expression vectors, a laboratory manual*. W. H. Freeman and Company, New York, N.Y.) was used to infect SF9 cells grown in suspension culture for 48 h at 27° C. (MOI of 1). Infected SF9 cells were harvested by centrifugation, washed twice with ice cold Rinaldini's salt solution (Sigma Chemical Co., St. Louis, Mo.) containing 1.0 mM $CaCl_2$, and membranes were prepared as described (Hodgkin et al., *J. Immunol.* 145:2025. (1990), Brian, A. A. *Proc. Natl. Acad. Sci. USA* 85:564. (1988), Maeda, T., et al., *Biochim. Biophy. Acta* 731:115 (1983)). Membranes, hdmb human CD40 ligand, were washed and resuspended in Dulbecco's PBS and stored under liquid nitrogen. Total membrane protein concentration was determined for each preparation (Micro BCA assay, Pierce). Batches of membranes were titrated in a B cell proliferation assay (see below).

Flow cytometry. Expression of CD40 ligand on the surface of SF9 insect cells was quantitated by flow cytometry. SF9 cells infected for various times with a baculovirus recombinant for human CD40 ligand were washed in insect FACS buffer (Rinaldini's salt solution containing 2% BSA and 0.2% sodium azide) and preincubated 30 min at 4° C. with 5 $\mu$g/ml nonspecific mouse IgG1 in insect FACS buffer. Cells were stained with 10 $\mu$g/ml CD40-IgG1 (Castle, et al., *J. Immunol.* 151:1777 (1993)) or control human IgG1 followed by biotinylated monoclonal mouse anti-human IgG1 (10 $\mu$g/ml; Zymed) and phycoerythrin (PE)-streptavidin (20 $\mu$g/ml; Jackson ImmunoResearch). All staining was in insect FACS buffer containing 5 $\mu$g/ml nonspecific mouse IgG1. Fluorescence was analyzed in a log single color mode on a FACScan flow cytometer (Becton Dickinson, San Jose, Calif.).

Preparation of human B cells. Human peripheral blood mononuclear cells obtained after centrifugation over Ficoll-Hypaque were incubated with biotinylated anti-CD19 (CellPro, Bothell, Wash.), bound to avidin-conjugated beads (CEPRATE LC-19 column; CellPro), and eluted according to the manufacturer's instructions. Eluted cells were panned on petri dishes coated overnight with 5 $\mu$g/ml each anti-CD3 and anti-CD14. Nonadherent cells ($\sim 1 \times 10^6$/100 ml blood) were 84% to 93% B cells as assessed by dual staining with PE-anti-CD3 and FITC-anti-CD19 and by dual staining with PE-anti-CD20 and FITC-anti-IgM as described previously (Kehry, et al., *Cell. Immunol.* 118:504 (1989)). Fluorescence was analyzed in a log two color mode on a FACScan flow cytometer. B cells can also be isolated from tonsil, spleen, and bone marrow by similar techniques or by sorting on a flow cytometer after staining with fluorescently labeled anti-CD19 or anti-CD20 or specific antigen.

B cell assays. For proliferation studies, B cells (between $5 \times 10^3$ and $1 \times 10^4$/well) were incubated for 96 h at 37° C. with serial dilutions of membranes in 100 $\mu$l BCM (Falcon 3072 96-well microtiter plates). Final concentrations of recombinant lymphokines used were 1 ng/ml IL-1$\alpha$, 5 ng/ml IL-11, and 10 ng/ml each, IL-2, IL-4, IL-6, and IL-10. During the last 6 h of culture, [methyl, 1',2'-$^3$H]thymidine (120 Ci/mmol; Amersham, Arlington Heights, Ill.) was added (1 $\mu$Ci/well). Cultures were harvested on an automated 96-well cell harvester (Tomtec, Orange, Conn.) for scintillation counting (Beckman, Fullerton, Calif.). Measurement of viable B cell numbers was accomplished by cell counting. Cells from triplicate wells were combined, harvested by centrifugation, resuspended in 50 $\mu$l BCM, and mixed with an equal volume of 0.4% trypan blue in 0.85% NaCl. Live cells were counted under a hemocytometer and an average number for the replicate wells was calculated.

For long term growth experiments, B cells ($5 \times 10^2$ or $1 \times 10^3$/well) were cultured in V-bottom 96 well microtiter plates (001-010-2701, Dynatech Laboratories, Inc., Chantilly, Va.) in 150 µl BCM at 37° C., 5.5% $CO_2$. hdmb human CD40 ligand and T cell supernatants containing lymphokines were added at the indicated concentrations; recombinant lymphokines were added at the concentrations listed above. Culture wells were fed fresh medium components on the days indicated as follows. Plates were centrifuged at 1600 rpm for 7 min (GS-6KR centrifuge, Beckman), medium was aspirated leaving ~15 µl, and fresh medium (150 µl) was added.

IgM and IgG levels were measured by isotype-specific sandwich ELISA as described previously (Hodgkin, et al, Eur. J. Immunol. 24:239 (1994)) using the reagents described above. Monoclonal human IgM (50 ng/ml) and equimolar mixtures of monoclonal human IgG1, IgG2, IgG3, and IgG4 (50 ng/ml total) were used as standards. Culture media samples (140 µl/well) were harvested from replicate wells of growing B cells.

ELISPOT assays to detect antigen-specific antibody secreting cells were as described previously (Hodgkin, et al., Eur. J. Immunol. 24:239 (1994), Czerkinsky, et al. J. Immunol. Methods 110:29 (1988)). Multiscreen-HA filter bottom 96 well plates (Millipore, Bedford, Mass.) were coated with 5 µg/ml KLH overnight at 4° C. Plates containing growing B cells were centrifuged and the cells washed twice prior to resuspending in 100 µl fresh BCM. Cells from each well were transferred in duplicate to coated Multiscreen plates and incubated in 100 µl BCM/well for 16 h at 37° C. Plates were developed using biotinylated anti-mouse IgM or anti-mouse IgG reagents as described previously (Hodgkin, et al., Eur. J. Immunol. 24:239 (1994)). After stopping the reaction, wells were allowed to dry in the dark for several days, and the spots corresponding to specific IgM or IgG antibody were enumerated under a dissecting microscope.

Results

Human CD40 ligand in insect cell membranes stimulates efficient human B cell proliferation Optimal expression of human CD40 ligand in SF9 insect cells was determined by infecting SF9 cells for various times with a recombinant baculovirus and quantitating expression levels by flow cytometry. Expression of human CD40 ligand was found to be maximal after 48 h of infection. An enriched plasma membrane fraction was prepared from 48 h infected SF9 cells and used in subsequent experiments (hdmb human CD40 ligand). Purified human B cells proliferated efficiently in response to hdmb human CD40 ligand, and the response was enhanced by including a mixture of recombinant human IL-1a, IL-2, IL-4, IL-6, IL-10, and IL-11 (FIG. 11). In the absence of hdmb human CD40 ligand human B cells did not divide (FIG. 11).

Clonal frequency of human B cell growth and differentiation

Figure 12B:
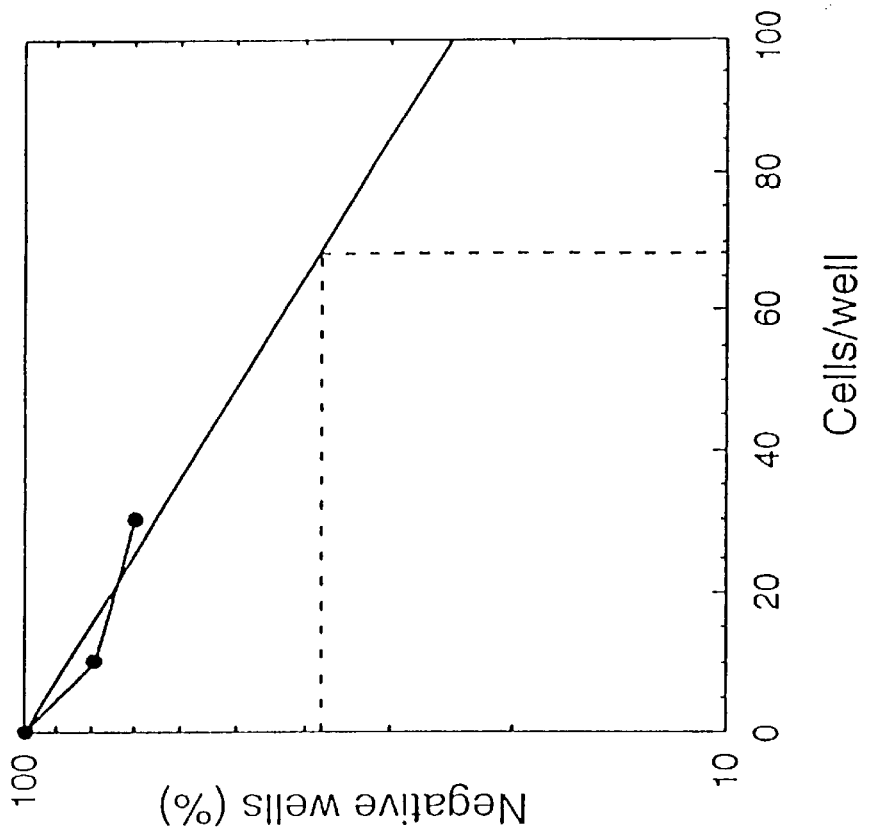
Figure 12A:
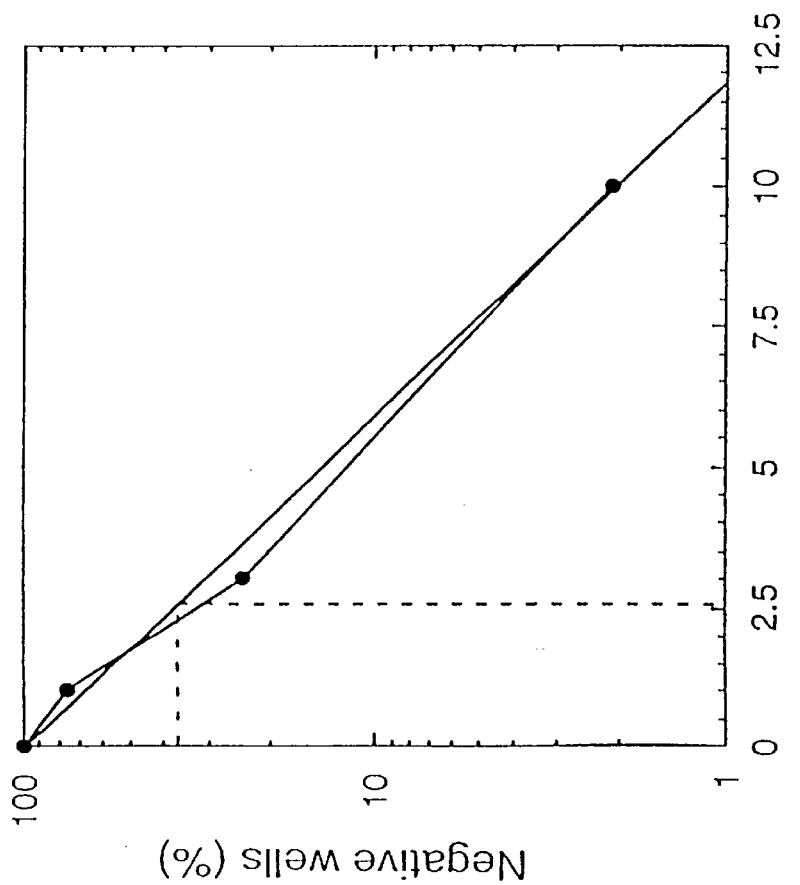

A frequency analysis of responding B cells plated at limiting dilution showed that after 14 days, approximately 1 in 2.5 B cells grew in response to hdmb human CD40 ligand and the mixture of recombinant human lymphokines used above (FIG. 12A). Many B cell clones contained approximately 20 to 50 cells. To obtain the frequency of B cell differentiation culture supernatants from the limiting dilution, cultures were harvested at day 11 and screened by ELISA for the presence of human IgM and IgG. Approximately 1 in 70 B cells differentiated to secrete either IgM or IgG in response to hdmb human CD40 ligand and recombinant human lymphokines (FIG. 12B). Together with the frequency of growth, this implies that approximately 1 in 28 B cells that grew differentiated to secrete antibody.

Optimization of human B cell differentiation to immunoglobulin secretion

Since the frequency of clonal growth of human B cells in response to hdmb human CD40 ligand was very similar to that of mouse splenic B cells, possibilities for the differing frequencies of immunoglobulin secretion between the two species of B cells were either the B cell source (peripheral blood versus spleen) or the lymphokines required (recombinant lymphokines versus supernatant from activated helper T cells). To optimize the lymphokines required for human B cell differentiation, supernatants were prepared from peripheral blood T cells activated for 48 h with either immobilized anti-CD3 or a pulse of PHA and PMA. The human T cell supernatants were tested for the ability to support differentiation of human B cells stimulated by hdmb human CD40 ligand. The supernatants were tested in the presence or absence of additional recombinant human lymphokines. Lymphokines secreted by PHA- and PMA-activated T cells did not support differentiation of hdmb human CD40 ligand-stimulated B cells and were inhibitory when added to a combination of recombinant human IL-2, IL-4, IL-6, and IL-10 (FIG. 13). In contrast, lymphokines secreted by anti-CD3-activated T cells supported differentiation of hdmb human CD40 ligand-stimulated B cells as well as recombinant lymphokines. Slightly lower levels of IgM and higher levels of IgG were produced by B cells stimulated by hdmb human CD40 ligand and anti-CD3 supernatant relative to cells stimulated with hdmb human CD40 ligand and recombinant IL-2, IL-4, IL-6, and IL-10 (FIG. 13). The amounts of IGM and IgG produced by hdmb human CD40 ligand-stimulated human B cells increased in a dose-dependent fashion with increasing amounts of lymphokines secreted by anti-CD3 activated T cells (FIG. 14). Additionally, IgM and IgG production appeared to be dependent on the presence of lymphokines and was undetectable in the presence of hdmb human CD40 ligand alone. The levels of human immunoglobulin production obtained in the experiment depicted in FIGS. 13 and 14, although ~10-fold lower than that produced by mouse splenic B cells stimulated under analogous conditions, are similar to levels of human immunoglobulin reported in the literature to be secreted by 20- to 100-fold higher numbers of human B cells (Rousset,et al., J. Exp. Med. 173, :705 (1991), Armitage, et al., J. Immunol. 150:3671(1993), Nonoyama, et al., J. Exp. Med. 178:1097 (1993)).

Frequency of antigen-specific B cell differentiation in an unprimed population

A goal of this work is to expand antigen-specific B cell clones for the subsequent isolation of antigen-specific antibody. To assess the frequency of antigen-specific B cells in an unprimed population of cells, mouse splenic B cells were plated at limiting dilution in the presence of a suboptimal dose of hdmb mouse CD40 ligand and D10 supernatant and the frequency of KLH-specific antibody secreting cells was measured after 14 days. Approximately 1 in 2500 cells secreted KLH-specific IgM and 1 in 10,000 cells secreted KLH-specific IgG (FIG. 15). These frequencies are as expected from analyzing culture supernatants from random wells plated at 1000 cells/well for KLH-specific antibodies (1 in 8 positive).

This finding demonstrates that, given the high frequency of B cells responding to hdmb human CD40 ligand and lymphokines, antigen-specific responding cells can be identified at a reasonable frequency in B cell preparations containing as few as $1 \times 10^6$ cells. Additionally, the ELISPOT method used to identify antigen-specific antibody secreting B cells can be modified to isolate antigen-specific B cells by panning on antigen-coated wells. In this fashion, expanded B cells can be recovered by virtue of the specificity of their surface immunoglobulin regardless of whether they have differentiated to immunoglobulin secretion.

What is claimed is:

1. A method of proliferating B cells comprising:
providing a high density, membrane bound CD40 ligand; and
culturing one or more B cells in the presence of said high density, membrane bound CD40 ligand;
wherein said culturing results in a proliferation in the number of said B cells of at least 100-fold.

2. A method for differentiating proliferating B cells into antibody producing cells comprising:
providing a high density, membrane bound CD40 ligand; and
culturing one or more B cells in the presence of one or more cytokines and said high density, membrane bound CD40 ligand;
wherein said culturing results in a proliferation in the number of said B cells of at least 100-fold.

3. The method of claim 1, wherein said high density, membrane bound CD40 ligand is produced by culturing insect cells transfected with an expression vector comprising a nucleotide sequence encoding CD40 ligand.

4. The method of claim 1, wherein said B cells are human B cells.

5. The method of claim 2, wherein said cytokines are Th2 lymphokines capable of differentiating proliferating B cells into antibody producing cells.

6. The method of claim 2, wherein said cytokines are recombinant human Interleukin-1α (IL-1α), IL-2, IL-4, IL-6, IL-10 and IL-11.

7. The method of claim 2, wherein said cytokines is the supernatant from anti-CD3 stimulated human peripheral blood T-cells.

8. The method of claim 2, wherein said B cells are incubated in the presence of an antigen during proliferation.

9. The method of claim 8, wherein a multistep procedure for culturing B cells is used, comprising a resting stage and a proliferation stage; and said antigen is added during a resting phase of said multistep culturing procedure.

10. The method of claim 8, wherein said antigen is covalently attached to a membrane containing said high density, membrane bound CD40 ligand.

11. The method of claim 1, wherein said culturing step results in a proliferation in the number of said B cells of at least 250-fold.

12. The method of claim 2, wherein said culturing step results in a proliferation in the number of said B cells of at least 250-fold.

13. The method of claim 1, wherein said culturing of one or more B cells results in about 8 rounds of division over 6 days.

14. The method of claim 2, wherein said culturing of one or more B cells results in about 8 rounds of division over 6 days.

* * * * *

UNITED STATES PATENT AND TRADEMARK OFFICE
CERTIFICATE OF CORRECTION

PATENT NO. : 5,817,516

DATED : October 6, 1998

INVENTORS : Kehry *et al.*

It is certified that an error appears in the above-identified patent and that said Letters Patent is hereby corrected as shown below.

In the Claims, column 37, line 57, please delete "of" and insert therein --for--.

In the Claims, column 39, line 7, please delete "is" and insert therein --are in--.

In the Claims, column 39, line 13, after "culturing" please insert therein --said--.

Signed and Sealed this

Second Day of March, 1999

Attest:

Q. TODD DICKINSON

*Attesting Officer*    *Acting Commissioner of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 818 base pairs
        ( B ) TYPE: nucleic acid
        ( C ) STRANDEDNESS: both
        ( D ) TOPOLOGY: linear ( i i ) MOLECULE TYPE: DNA ( i x ) FEATURE:
        ( A ) NAME/KEY: CDS
        ( B ) LOCATION: 13..795

( x i ) SEQUENCE DESCRIPTION: SEQ ID NO:1:

```
CTTTCAGTCA GC ATG ATA GAA ACA TAC AGC CAA CCT TCC CCC AGA TCC         48
              Met Ile Glu Thr Tyr Ser Gln Pro Ser Pro Arg Ser
                1               5                  10

GTG GCA ACT GGA CTT CCA GCG AGC ATG AAG ATT TTT ATG TAT TTA CTT       96
Val Ala Thr Gly Leu Pro Ala Ser Met Lys Ile Phe Met Tyr Leu Leu
        15              20                  25

ACT GTT TTC CTT ATC ACC CAA ATG ATT GGA TCT GTG CTT TTT GCT GTG      144
Thr Val Phe Leu Ile Thr Gln Met Ile Gly Ser Val Leu Phe Ala Val
    30              35                  40

TAT CTT CAT AGA AGA TTG GAT AAG GTC GAA GAG GAA GTA AAC CTT CAT      192
Tyr Leu His Arg Arg Leu Asp Lys Val Glu Glu Glu Val Asn Leu His
45              50                  55                        60

GAA GAT TTT GTA TTC ATA AAA AAG CTA AAG AGA TGC AAC AAA GGA GAA      240
Glu Asp Phe Val Phe Ile Lys Lys Leu Lys Arg Cys Asn Lys Gly Glu
                65                  70                  75

GGA TCT TTA TCC TTG CTG AAC TGT GAG GAG ATG AGA AGG CAA TTT GAA      288
Gly Ser Leu Ser Leu Leu Asn Cys Glu Glu Met Arg Arg Gln Phe Glu
            80                  85                  90

GAC CTT GTC AAG GAT ATA ACG TTA AAC AAA GAA GAG AAA AAA GAA AAC      336
Asp Leu Val Lys Asp Ile Thr Leu Asn Lys Glu Glu Lys Lys Glu Asn
        95                  100                 105

AGC TTT GAA ATG CAA AGA GGT GAT GAG GAT CCT CAA ATT GCA GCA CAC      384
Ser Phe Glu Met Gln Arg Gly Asp Glu Asp Pro Gln Ile Ala Ala His
    110                 115                 120

GTT GTA AGC GAA GCC AAC AGT AAT GCA GCA TCC GTT CTA CAG TGG GCC      432
Val Val Ser Glu Ala Asn Ser Asn Ala Ala Ser Val Leu Gln Trp Ala
125                 130                 135                 140

AAG AAA GGA TAT TAT ACC ATG AAA AGC AAC TTG GTA ATG CTT GAA AAT      480
Lys Lys Gly Tyr Tyr Thr Met Lys Ser Asn Leu Val Met Leu Glu Asn
                145                 150                 155

GGG AAA CAG CTG ACG GTT AAA AGA GAA GGA CTC TAT TAT GTC TAC ACT      528
Gly Lys Gln Leu Thr Val Lys Arg Glu Gly Leu Tyr Tyr Val Tyr Thr
            160                 165                 170

CAA GTC ACC TTC TGC TCT AAT CGG GAG CCT TCG AGT CAA CGC CCA TTC      576
Gln Val Thr Phe Cys Ser Asn Arg Glu Pro Ser Ser Gln Arg Pro Phe
        175                 180                 185

ATC GTC GGC CTC TGG CTG AAG CCC AGC ATT GGA TCT GAG AGA ATC TTA      624
Ile Val Gly Leu Trp Leu Lys Pro Ser Ile Gly Ser Glu Arg Ile Leu
    190                 195                 200

CTC AAG GCG GCA AAT ACC CAC AGT TCC TCC CAG CTT TGC GAG CAG CAG      672
Leu Lys Ala Ala Asn Thr His Ser Ser Ser Gln Leu Cys Glu Gln Gln
205                 210                 215                 220
```

| | | | | | | | | | | | | | | | |
|---|---|---|---|---|---|---|---|---|---|---|---|---|---|---|---|
| TCT | GTT | CAC | TTG | GGC | GGA | GTG | TTT | GAA | TTA | CAA | GCT | GGT | GCT | TCT | GTG | 720
| Ser | Val | His | Leu | Gly | Gly | Val | Phe | Glu | Leu | Gln | Ala | Gly | Ala | Ser | Val |
| | | | 225 | | | | | 230 | | | | | | 235 | |
| TTT | GTC | AAC | GTG | ACT | GAA | GCA | AGC | CAA | GTG | ATC | CAC | AGA | GTT | GGC | TTC | 768
| Phe | Val | Asn | Val | Thr | Glu | Ala | Ser | Gln | Val | Ile | His | Arg | Val | Gly | Phe |
| | | | 240 | | | | | 245 | | | | | | 250 | |
| TCA | TCT | TTT | GGC | TTA | CTC | AAA | CTC | TGAACAGTGC | GCTGTCCTAG | GCTGCA | | | | | | 818
| Ser | Ser | Phe | Gly | Leu | Leu | Lys | Leu | | | | | | | | |
| | | 255 | | | | | 260 | | | | | | | | |

( 2 ) INFORMATION FOR SEQ ID NO:2:

( i ) SEQUENCE CHARACTERISTICS:
        ( A ) LENGTH: 260 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Ile | Glu | Thr | Tyr | Ser | Gln | Pro | Ser | Pro | Arg | Ser | Val | Ala | Thr | Gly |
| 1 | | | | 5 | | | | | 10 | | | | | 15 | |
| Leu | Pro | Ala | Ser | Met | Lys | Ile | Phe | Met | Tyr | Leu | Leu | Thr | Val | Phe | Leu |
| | | | 20 | | | | | 25 | | | | | 30 | | |
| Ile | Thr | Gln | Met | Ile | Gly | Ser | Val | Leu | Phe | Ala | Val | Tyr | Leu | His | Arg |
| | | 35 | | | | | 40 | | | | | 45 | | | |
| Arg | Leu | Asp | Lys | Val | Glu | Glu | Val | Asn | Leu | His | Glu | Asp | Phe | Val |
| | 50 | | | | | 55 | | | | | 60 | | | | |
| Phe | Ile | Lys | Lys | Leu | Lys | Arg | Cys | Asn | Lys | Gly | Glu | Gly | Ser | Leu | Ser |
| 65 | | | | | 70 | | | | | 75 | | | | | 80 |
| Leu | Leu | Asn | Cys | Glu | Glu | Met | Arg | Arg | Gln | Phe | Glu | Asp | Leu | Val | Lys |
| | | | | 85 | | | | | 90 | | | | | 95 | |
| Asp | Ile | Thr | Leu | Asn | Lys | Glu | Glu | Lys | Lys | Glu | Asn | Ser | Phe | Glu | Met |
| | | | 100 | | | | | 105 | | | | | 110 | | |
| Gln | Arg | Gly | Asp | Glu | Asp | Pro | Gln | Ile | Ala | Ala | His | Val | Val | Ser | Glu |
| | | 115 | | | | | 120 | | | | | 125 | | | |
| Ala | Asn | Ser | Asn | Ala | Ala | Ser | Val | Leu | Gln | Trp | Ala | Lys | Lys | Gly | Tyr |
| | 130 | | | | | 135 | | | | | 140 | | | | |
| Tyr | Thr | Met | Lys | Ser | Asn | Leu | Val | Met | Leu | Glu | Asn | Gly | Lys | Gln | Leu |
| 145 | | | | | 150 | | | | | 155 | | | | | 160 |
| Thr | Val | Lys | Arg | Glu | Gly | Leu | Tyr | Tyr | Val | Tyr | Thr | Gln | Val | Thr | Phe |
| | | | | 165 | | | | | 170 | | | | | 175 | |
| Cys | Ser | Asn | Arg | Glu | Pro | Ser | Ser | Gln | Arg | Pro | Phe | Ile | Val | Gly | Leu |
| | | | 180 | | | | | 185 | | | | | 190 | | |
| Trp | Leu | Lys | Pro | Ser | Ile | Gly | Ser | Glu | Arg | Ile | Leu | Leu | Lys | Ala | Ala |
| | | 195 | | | | | 200 | | | | | 205 | | | |
| Asn | Thr | His | Ser | Ser | Ser | Gln | Leu | Cys | Glu | Gln | Gln | Ser | Val | His | Leu |
| | 210 | | | | | 215 | | | | | 220 | | | | |
| Gly | Gly | Val | Phe | Glu | Leu | Gln | Ala | Gly | Ala | Ser | Val | Phe | Val | Asn | Val |
| 225 | | | | | 230 | | | | | 235 | | | | | 240 |
| Thr | Glu | Ala | Ser | Gln | Val | Ile | His | Arg | Val | Gly | Phe | Ser | Ser | Phe | Gly |
| | | | | 245 | | | | | 250 | | | | | 255 | |
| Leu | Leu | Lys | Leu | | | | | | | | | | | | |
| | | | 260 | | | | | | | | | | | | |

( 2 ) INFORMATION FOR SEQ ID NO:3:

( i ) SEQUENCE CHARACTERISTICS:
        ( A ) LENGTH: 840 base pairs 5,817,516

35 36

-continued ( B ) TYPE: nucleic acid
( C ) STRANDEDNESS: both
( D ) TOPOLOGY: linear ( i i ) MOLECULE TYPE: DNA ( i x ) FEATURE:
   ( A ) NAME/KEY: CDS
   ( B ) LOCATION: 22..807

( x i ) SEQUENCE DESCRIPTION: SEQ ID NO:3:

```
CCATTTCAAC TTTAACACAG C ATG ATC GAA ACA TAC AAC CAA ACT TCT CCC          51
                       Met Ile Glu Thr Tyr Asn Gln Thr Ser Pro
                        1               5                   10

CGA TCT GCG GCC ACT GGA CTG CCC ATC AGC ATG AAA ATT TTT ATG TAT          99
Arg Ser Ala Ala Thr Gly Leu Pro Ile Ser Met Lys Ile Phe Met Tyr
             15                  20                  25

TTA CTT ACT GTT TTT CTT ATC ACC CAG ATG ATT GGG TCA GCA CTT TTT         147
Leu Leu Thr Val Phe Leu Ile Thr Gln Met Ile Gly Ser Ala Leu Phe
         30                  35                  40

GCT GTG TAT CTT CAT AGA AGG TTG GAC AAG ATA GAA GAT GAA AGG AAT         195
Ala Val Tyr Leu His Arg Arg Leu Asp Lys Ile Glu Asp Glu Arg Asn
     45                  50                  55

CTT CAT GAA GAT TTT GTA TTC ATG AAA ACG ATA CAG AGA TGC AAC ACA         243
Leu His Glu Asp Phe Val Phe Met Lys Thr Ile Gln Arg Cys Asn Thr
 60                  65                  70

GGA GAA AGA TCC TTA TCC TTA CTG AAC TGT GAG GAG ATT AAA AGC CAG         291
Gly Glu Arg Ser Leu Ser Leu Leu Asn Cys Glu Glu Ile Lys Ser Gln
 75                  80                  85                  90

TTT GAA GGC TTT GTG AAG GAT ATA ATG TTA AAC AAA GAG GAG ACG AAG         339
Phe Glu Gly Phe Val Lys Asp Ile Met Leu Asn Lys Glu Glu Thr Lys
             95                  100                 105

AAA GAA AAC AGC TTT GAA ATG CAA AAA GGT GAT CAG AAT CCT CAA ATT         387
Lys Glu Asn Ser Phe Glu Met Gln Lys Gly Asp Gln Asn Pro Gln Ile
             110                 115                 120

GCG GCA CAT GTC ATA AGT GAG GCC AGC AGT AAA ACA ACA TCT GTG TTA         435
Ala Ala His Val Ile Ser Glu Ala Ser Ser Lys Thr Thr Ser Val Leu
         125                 130                 135

CAG TGG GCT GAA AAA GGA TAC TAC ACC ATG AGC AAC AAC TTG GTA ACC         483
Gln Trp Ala Glu Lys Gly Tyr Tyr Thr Met Ser Asn Asn Leu Val Thr
     140                 145                 150

CTG GAA AAT GGG AAA CAG CTG ACC GTT AAA AGA CAA GGA CTC TAT TAT         531
Leu Glu Asn Gly Lys Gln Leu Thr Val Lys Arg Gln Gly Leu Tyr Tyr
155                 160                 165                 170

ATC TAT GCC CAA GTC ACC TTC TGT TCC AAT CGG GAA GCT TCG AGT CAA         579
Ile Tyr Ala Gln Val Thr Phe Cys Ser Asn Arg Glu Ala Ser Ser Gln
             175                 180                 185

GCT CCA TTT ATA GCC AGC CTC TGC CTA AAG TCC CCC GGT AGA TTC GAG         627
Ala Pro Phe Ile Ala Ser Leu Cys Leu Lys Ser Pro Gly Arg Phe Glu
             190                 195                 200

AGA ATC TTA CTC AGA GCT GCA AAT ACC CAC AGT TCC GCC AAA CCT TGC         675
Arg Ile Leu Leu Arg Ala Ala Asn Thr His Ser Ser Ala Lys Pro Cys
         205                 210                 215

GGG CAA CAA TCC ATT CAC TTG GGA GGA GTA TTT GAA TTG CAA CCA GGT         723
Gly Gln Gln Ser Ile His Leu Gly Gly Val Phe Glu Leu Gln Pro Gly
         220                 225                 230

GCT TCG GTG TTT GTC AAT GTG ACT GAT CCA AGC CAA GTG AGC CAT GGC         771
Ala Ser Val Phe Val Asn Val Thr Asp Pro Ser Gln Val Ser His Gly
235                 240                 245                 250

ACT GGC TTC ACG TCC TTT GGC TTA CTC AAA CTC TGAACAGTGT CACCTTGCAG       824
Thr Gly Phe Thr Ser Phe Gly Leu Leu Lys Leu
             255                 260
```

-continued

```
GCTGTGGTGG AGCTGA                                                                840
```

( 2 ) INFORMATION FOR SEQ ID NO:4:

( i ) SEQUENCE CHARACTERISTICS:
        ( A ) LENGTH: 261 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Ile Glu Thr Tyr Asn Gln Thr Ser Pro Arg Ser Ala Ala Thr Gly
 1           5                  10                  15
Leu Pro Ile Ser Met Lys Ile Phe Met Tyr Leu Leu Thr Val Phe Leu
            20                  25                  30
Ile Thr Gln Met Ile Gly Ser Ala Leu Phe Ala Val Tyr Leu His Arg
            35              40                  45
Arg Leu Asp Lys Ile Glu Asp Glu Arg Asn Leu His Glu Asp Phe Val
        50              55                  60
Phe Met Lys Thr Ile Gln Arg Cys Asn Thr Gly Glu Arg Ser Leu Ser
 65                 70                  75                  80
Leu Leu Asn Cys Glu Glu Ile Lys Ser Gln Phe Glu Gly Phe Val Lys
            85                  90                  95
Asp Ile Met Leu Asn Lys Glu Glu Thr Lys Lys Glu Asn Ser Phe Glu
            100                 105                 110
Met Gln Lys Gly Asp Gln Asn Pro Gln Ile Ala Ala His Val Ile Ser
        115                 120                 125
Glu Ala Ser Ser Lys Thr Thr Ser Val Leu Gln Trp Ala Glu Lys Gly
    130                 135                 140
Tyr Tyr Thr Met Ser Asn Asn Leu Val Thr Leu Glu Asn Gly Lys Gln
145                 150                 155                 160
Leu Thr Val Lys Arg Gln Gly Leu Tyr Tyr Ile Tyr Ala Gln Val Thr
                165                 170                 175
Phe Cys Ser Asn Arg Glu Ala Ser Ser Gln Ala Pro Phe Ile Ala Ser
            180                 185                 190
Leu Cys Leu Lys Ser Pro Gly Arg Phe Glu Arg Ile Leu Leu Arg Ala
        195                 200                 205
Ala Asn Thr His Ser Ser Ala Lys Pro Cys Gly Gln Gln Ser Ile His
    210                 215                 220
Leu Gly Gly Val Phe Glu Leu Gln Pro Gly Ala Ser Val Phe Val Asn
225                 230                 235                 240
Val Thr Asp Pro Ser Gln Val Ser His Gly Thr Gly Phe Thr Ser Phe
                245                 250                 255
Gly Leu Leu Lys Leu
            260
```